US011427621B2

(12) United States Patent
Soucek et al.

(10) Patent No.: US 11,427,621 B2
(45) Date of Patent: Aug. 30, 2022

(54) METHODS AND COMPOSITIONS FOR THE TREATMENT OF CANCER

(71) Applicants: FUNDACIÓ PRIVADA INSTITUT D'INVESTIGACIÓ ONCOLÒGICA DE VALL HEBRON, Barcelona (ES); INSTITUCIÓ CATALANA DE RECERCA I ESTUDIS AVANCATS, Barcelona (ES)

(72) Inventors: Laura Soucek, Barcelona (ES); Toni Jauset González, Barcelona (ES); Marie-Eve Beaulieu, Barcelona (ES)

(73) Assignees: INSTITUCIO CATALANA DE RECERCA I ESTUDIS AVANCATS, Barcelona (ES); FUNDACIO PRIVADA INSTITUT D'INVESTIGACIO ONCOLOGICA DE VALL HEBRON, Barcelona (ES)

( * ) Notice: Subject to any disclaimer, the term of this patent is extended or adjusted under 35 U.S.C. 154(b) by 825 days.

(21) Appl. No.: 16/317,850

(22) PCT Filed: Jul. 17, 2017

(86) PCT No.: PCT/EP2017/067998
§ 371 (c)(1),
(2) Date: Jan. 15, 2019

(87) PCT Pub. No.: WO2018/011433
PCT Pub. Date: Jan. 18, 2018

(65) Prior Publication Data
US 2020/0247857 A1    Aug. 6, 2020

(30) Foreign Application Priority Data
Jul. 15, 2016   (EP) ..................... 16382339

(51) Int. Cl.
*C07K 14/47*    (2006.01)
*A61K 47/62*    (2017.01)
*A61K 38/00*    (2006.01)

(52) U.S. Cl.
CPC .......... *C07K 14/4703* (2013.01); *A61K 47/62* (2017.08); *A61K 38/00* (2013.01)

(58) Field of Classification Search
None
See application file for complete search history.

(56) References Cited

U.S. PATENT DOCUMENTS

| | | | |
|---|---|---|---|
| 6,395,713 B1 | 5/2002 | Beigelman et al. | |
| 6,447,796 B1 | 9/2002 | Vook et al. | |
| 10,370,434 B2 * | 8/2019 | Soucek | .......... A61K 45/06 |
| 2001/0007666 A1 | 7/2001 | Hoffman et al. | |
| 2002/0130430 A1 | 9/2002 | Castor | |
| 2003/0027314 A1 | 2/2003 | Vinson et al. | |
| 2003/0077829 A1 | 4/2003 | MacLachlan | |
| 2016/0122415 A1 | 5/2016 | Soucek | |
| 2019/0382468 A1 * | 12/2019 | Soucek | .......... A61P 35/00 |

FOREIGN PATENT DOCUMENTS

| | | |
|---|---|---|
| EP | 0143949 | 6/1985 |
| EP | 0088046 | 12/1987 |
| EP | 0036676 | 9/1990 |
| EP | 0052322 | 3/1998 |
| EP | 2801370 | 11/2014 |
| WO | WO1994002595 | 2/1994 |
| WO | WO2000053722 | 9/2000 |
| WO | WO2003046185 | 6/2003 |
| WO | WO2003047518 | 6/2003 |
| WO | WO2006135436 | 12/2006 |
| WO | WO2014180889 | 11/2014 |
| WO | WO2018011433 | 1/2018 |

OTHER PUBLICATIONS

PDF GenBank: AAX4223.1 (Mar. 21, 2005) Downloaded Nov. 19, 2021. (Year: 2005).*
Akhtar et al., "Cellular uptake and intracellular fate of antisense oligonucleotides", Trends in Cell Biology, vol. 2, May 1992 (pp. 139-144).
Altschul et al., "Basic Local Alignment Search Tool", J. Mol. Biol. vol. 215, 1990 (pp. 403-410).
Annibali et al., "Myc inhibition is effective against glioma and reveals a role for Myc in proficient mitosis", Nature Communications, Aug. 2014 (pp. 1-11).
Bordo et al., "Suggestions for "Safe" Residue Substitutions in Site-directed Mutagenesis", J. Mol. Biol. vol. 217, 1991 (pp. 721-729).
Cohen, "Naked DNA Points Way to Vaccines", Science, vol. 259, Mar. 1993 (pp. 1691-1692).
Dang et al., "Identification of the human c-myc protein nuclear translocation signal", Mol. Cell. Biol. vol. 8(10), 1988 (pp. 4048-4054).
Eppstein et al., "Biological activity of liposome-encapsulated murine interferon γ is mediated by a cell membrane receptor", Proc. Natl. Sci. USA, vol. 82, 1985, (pp. 3688-3692).
Gonzalez et al., "New Class of Polymers for the Delivery of Macromolecular Therapeutics", Bioconjugate Chem. vol. 10, 1999, (pp. 1068-1074).
Gorlich, "Transport into and out of the cell nucleus", The EMBO Journal, vol. 17, No. 10, 1998, (pp. 2721-2727).
Hofland et al., "Formulation and Delivery of Nucleic Acids", Handb Exp. Pharmacol. 1999, (pp. 165-192).
Hwang et al., "Hepatic uptake and degradation of unilamellar sphingomyelin/cholesterol liposomes: A kinetic study", Proc. Natl. Acad. Sci. USA, vol. 77, No. 7, 1980, (pp. 4030-4034).

(Continued)

Primary Examiner — Anand U Desai
(74) Attorney, Agent, or Firm — Dechert LLP; Andrea L. C. Reid; Gang Wang

(57) ABSTRACT

The invention relates to a polypeptide comprising or consisting of the polypeptide of SEQ ID NO: 1 wherein the residue X at position 89 of SEQ ID NO: 1 is not a cysteine, or a functionally equivalent variant of said polypeptide wherein the residue X at position 89 of SEQ ID NO: 1 is not a cysteine and their use in medicine, particularly in the prevention and/or treatment of cancer.

20 Claims, 2 Drawing Sheets
Specification includes a Sequence Listing.

(56) References Cited

OTHER PUBLICATIONS

Jung et al., "OmoMYC blunts promoter invasion by oncogenic MYC to inhabit gene expression characteristic of MYC-dependent tumors", Oncogene, 2016 (pp. 1-14).
Lee et al., "Modified Liposome Formulations for Cytosolic delivery of Macromolecules", ACS Symp. Ser., 2000, (pp. 184-192).
Maurer et al., "Lipid-based systems for the intracellular delivery of genetic drugs", Mol. Membr. Biol., vol. 16:1, 1999, (pp. 129-140).
Nair et al., "X-Ray Structures of Myc-Max and Mad-Max Recognizing DNA, Molecular Bases of Regulation by Proto-Oncogenic Transcription Factors", Cell, vol. 112, 2003 (pp. 193-205).
Savino et al., "The Action Mechanism of the Myc Inhibitor termed Omomyc May Give Clues on How to Target Myc for Cancer Therapy", PLoS One, vol. 6, Issue 7, Jul. 2011, (pp. 1-16).
Selbo et al., Photochemical Internalisation: A Novel Drug Delivery System, Tumor Biol., vol. 23, 2002, (pp. 103-112).
Selbo et al., "Photochemical Internalisation Increases the Cytotoxic Effect of the Immunotoxin Moc3 1-gelonin", Int. J. Cancer, vol. 87, 2000, (pp. 853-859).
Sodir et al., "Endogenous Myc maintains the tumor microenvironment", Genes Dev., vol. 25, Mar. 2011, (pp. 907-916).
Soucek et al, "Design and properties of a Myc derivative that efficiently homodimerizes", Oncogene, vol. 17, 1998, (pp. 2463-2472).
Soucek et al., "Omomyc, a Potential Myc Dominant Negative, Enhances Myc-induced Apoptosis", Cancer Res. vol. 62, Jun. 2002, (pp. 2507-3510).
Soucek et al., "Omomyc expression in skin prevents Myc-induced papillomatosis", Cell Death Differ., vol. 11, 2004, (pp. 1038-1045).
Soucek et al., "Modelling Myc inhibition as a cancer therapy", Nature, vol. 455, Oct. 2008, pp. 679-683.
Soucek et al., "Inhibition of Myc family proteins eradicates KRas-driven lung cancer in mice", Genes Dev., vol. 27, 2013 (pp. 504-513).
Taylor, "The Classification of Amino Acid Conservation", J. Theor. Biol., vol. 119, 1986, (pp. 205-218).
Terpe, "Overview of tag protein fusions: from molecular and biochemical fundamentals to commercial systems", Appl. Microbiol. Biotechnol., vol. 60, 2003, (pp. 523-533).
Thompson et al, "Clustal W: improving the sensitivity of progressive multiple sequence alignment through sequence weighting, positionspecific gap penalties and weight matrix choice", Nucleic Acid Res. vol. 22, No. 22, 1994, (pp. 4673-4680).
Travis et al., "Histological Typing of Lung and Pleural Tumours", World Health Org., Third Edition, 1999 (pp. 1-169).
Ulmer et al., "Heterologous Protection Against Influenza by Injection of DNA Encoding a Viral Protein", Science, vol. 259, Mar. 1993 (pp. 1745-1749).
Bidwell G.L. et al, "Targeting a c-Myc inhibitory polypeptide to specific intracellular compartments using cell penetrating peptides", Joural of Controlled Release, 2008, vol. 135(1); pp. 2-10.
Soucek et al., "Abstract 2923: Preclinical validation of Omomyc cell-penetrating peptides as a viable in vivo anti-Myc therapy", Proceedings of the 14th Annual Meeting of the American Association for Cancer Research; Jul. 2016; pp. 1-3.
Database REFSEQ_XP_003516054 May 27, 2016.
Database UNIPROT_G5B9M9, Mar. 16, 2016.
Database UNIPROT_Q6WDE6_ACOIG, Mar. 16, 2016.
PCT International Search Report from PCT/EP2017/067998, dated Oct. 23, 2017.

* cited by examiner

METHODS AND COMPOSITIONS FOR THE TREATMENT OF CANCER

FIELD OF THE INVENTION

The invention relates to the field of cancer and, more particularly, to polypeptides, compositions and their use in medicine, particularly in the prevention and/or treatment of cancer.

BACKGROUND OF THE INVENTION

The ideal cancer drug should target a non-redundant function continuously necessary for tumor maintenance, but dispensable for maintenance and function of any normal tissues. Hence, the most common logic is to target gene products that are specifically mutated in cancer, on the basis that these mutant molecules would be the likely "drivers" of the cancer and, perhaps, less critical for normal tissues. For these reasons, much attention has focused on cataloguing recurring lesions in specific cancer types. Unfortunately, there are several problems to this approach. First, most solid human cancers pass through episodes of genomic instability and exhibit a mutational noise that can obscure the "driver" mutations and their attendant effector pathways. Second, cancers are the end result of a process that involves transitions through multiple evolutionary bottlenecks. Each bottleneck may require a specific type of mutation whose function is thereafter dispensable for tumor maintenance and, consequently, not a good therapeutic target after that point in the tumor's evolution.

Myc is a basic helix-loop-helix leucine zipper (b-HLH-LZ) protein involved in growth control and cancer, which operates in a network with the structurally related proteins Max, Mad and Mnt. Myc/Max dimers activate gene transcription and induce cell proliferation or apoptosis. Mad/Max and Mnt/Max complexes act as repressors and cause cell growth arrest and differentiation. All dimers recognize the same DNA consensus site, the CACGTG E-box.

Myc is tightly regulated in normal cells, where its levels are higher in proliferating and lower in non-proliferating cells. Aberrantly high and/or deregulated Myc activity is causally implicated in most cancers and often associated with aggressive, poorly differentiated and angiogenic tumors. The deregulation of Myc expression is due to overexpression through gene amplifications, loss of transcriptional control, impaired degradation or increased stabilization. This results in aberrant proliferation, increased survival, changes in metabolism, angiogenesis and inflammation, all of which represent major hallmarks of cancer. Multiple studies substantiated the crucial role of Myc in governing intracellular and extracellular aspects of tumorigenesis suggesting that targeting its function would be therapeutically valuable.

It is known that down-regulation of Myc by a BET bromodomain inhibitor results in the regression of multiple tumor types. While this approach displays good potential, it presents some limitations such as toxicity and numerous off target effects. Many small molecules disrupting the Myc/Max interaction have displayed low specificity in cellulo.

A Myc inhibitor, however, has yet to become clinically available and its design presents various caveats: first, Myc is a nuclear transcription factor, which is consequently more difficult to reach than membrane or cytoplasmic molecules; second, Myc does not have an enzymatic "active site" that could be targeted; third, the Myc family comprises 3 different proteins, c-, N and L-Myc, which in certain conditions are functionally redundant, so all of them require simultaneous inhibition. Furthermore, there have been concerns that Myc inhibition would induce serious side effects by inhibiting proliferation of normal tissues. For all these reasons, making a Myc inhibitor drug is challenging.

Omomyc is a dominant-negative MYC mutant comprising the b-HLH-LZ domain of Myc and harboring four amino acid substitutions in the leucine zipper of Myc (Soucek, L. et al., 1998, Oncogene 17, 2463-2472; Soucek, L. et al. (2002), Cancer Res 62: 3507-3510). The amino acid substitutions E61T, E68I, R74Q, and R75N confer altered dimerization specificity to the protein, which retains the ability to bind its natural partner Max and to form homodimers with itself as well as heterodimers with wild type c-, N- and L-Myc.

Because of these properties, Omomyc is able to prevent Myc-dependent gene transactivation functions both in vitro and in vivo by negating the ability of Myc to bind its DNA recognition binding site, the E box. At the same time, Omomyc strongly potentiates Myc-induced apoptosis in a manner dependent on Myc expression level and thereby strengthens Myc transrepression activity. Omomyc thus prevents Myc binding to promoter E-boxes and transactivation of target genes while retaining Miz-1-dependent binding to promoters and transrepression. In the presence of Omomyc, the Myc interactome is channelled to repression and its activity switches from a pro-oncogenic to a tumor-suppressive one.

In EP2801370 A1 it was demonstrated that Omomyc peptide itself is capable of efficiently transducing across the cellular membrane and translocate to the nucleus, wherein it exerts its tumor-suppressive effect However, there is still a need in the state of the art to develop novel an improved therapeutic approaches for the treatment of cancer.

BRIEF SUMMARY OF THE INVENTION

In a first aspect, the invention refers to a polypeptide comprising the polypeptide of SEQ ID NO: 1 wherein the residue X at position 89 of SEQ ID NO: 1 is not a cysteine, or a functionally equivalent variant of said polypeptide wherein the residue X at position 89 of SEQ ID NO: 1 is not a cysteine.

In a second aspect, the invention relates to a conjugate comprising:
a. the polypeptide or functionally equivalent variant of said polypeptide according to the invention and
b. a chemical moiety that facilitates cellular uptake of the polypeptide or of the functionally equivalent variant of said polypeptide.

In a third aspect, the invention relates to a polynucleotide encoding a polypeptide according to the invention or a conjugate according to the invention.

In a fourth aspect, the invention relates to a vector comprising a polynucleotide according to the invention.

In a fifth aspect, the invention relates to a host cell comprising a polypeptide of the invention, a conjugate of the invention, a polynucleotide of the invention or a vector of the invention.

In a sixth aspect, the invention relates to a pharmaceutical composition comprising a pharmaceutically effective amount of a polypeptide or functional equivalent variant of said polypeptide according to the invention, a conjugate according to the invention, a polynucleotide according to the invention, a vector according to the invention or a host cell according to the invention, and a pharmaceutically acceptable excipient.

In a seventh aspect, the invention relates to a polypeptide or functional equivalent variant of said polypeptide according to the invention, a conjugate according to the invention, a polynucleotide according to the invention, a vector according to the invention, a host cell according to the invention or a pharmaceutical composition according to the invention for use in medicine.

In an eight aspect, the invention relates to a polypeptide or functional equivalent variant of said polypeptide according to the invention, a conjugate according to the invention, a polynucleotide according to the invention, a vector according to the invention, a host cell according to the invention or a pharmaceutical composition according to the invention for use in the prevention and/or treatment of cancer.

DETAILED DESCRIPTION OF THE INVENTION

Figure 1:
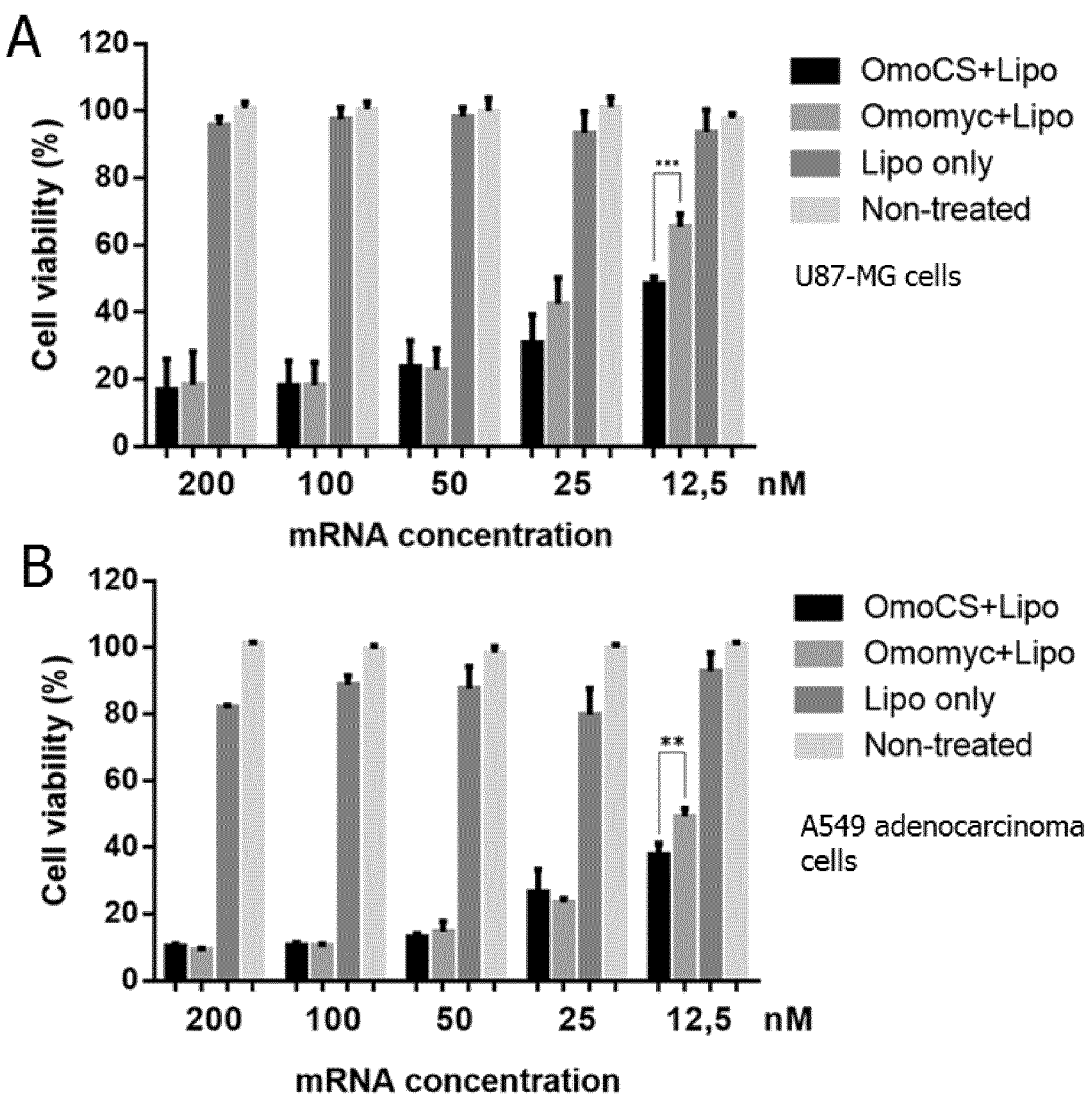
FIG. 1. Cell viability assay shows that OmoCS (harbouring the C89S change) inhibits the growth of U87 malignant glioma cells (A panel) and A549 lung adenocarcinoma cells (B panel) more efficiently than Omomyc (at lower concentration). Lipofectamine (Lipo) causes no effect. T-test was used to calculate statistical significance. =P<0.01, *=P<0.001

The authors of the present invention have found that a polypeptide of SEQ ID NO: 1, wherein the cysteine at position 89 is replaced by a serine, named as OmoCS, is capable of exerting its tumor suppressive effect more efficiently than Omomyc (Example 1). This tumor suppressive effect is maintained when the cysteine at position 89 of SEQ ID NO: 1 is replaced by other amino acids. Example 2 shows that a polypeptide of SEQ ID NO: 1, wherein the cysteine at position 89 is replaced by an alanine, named as OmoCA, has the same tumor suppressive effect as OmoCS.

Polypeptide of the Invention

Therefore, in a first aspect the invention relates to a polypeptide comprising the polypeptide of SEQ ID NO: 1 wherein the residue X at position 89 of SEQ ID NO: 1 is not a cysteine, or a functionally equivalent variant of said polypeptide wherein the residue X at position 89 of SEQ ID NO: 1 is not a cysteine.

The SEQ ID NO: 1 corresponds to (SEQ ID NO: 1)
TEENVKRRTHNVLERQRRNELKRSFFALRDQIPELENNEKAPKVVILKKA

TAYILSVQAETQKLISEIDLLRKQNEQLKHKLEQLRNSXA

The polypeptide of sequence SEQ ID NO: 1 corresponds to the Omomyc protein sequence, but the residue X at position 89 is not a cysteine. The term "Omomyc", as used herein, refers to a polypeptide which consists of a mutated version of the bHLHZip domain of the Myc protein carrying the E61T, E68I, R74Q and R75N mutations (wherein the numbering of the mutated positions is given with respect to the sequence of Myc region corresponding to amino acids 365-454 of the polypeptide as defined under accession number NP 002458 in the NCBI database, release of Mar. 15, 2015). The sequence of c-Myc provided in the NCBI database under the accession number NP_002458 is shown below (SEQ ID NO: 5), wherein the region from which Omomyc derives is shown underlined:

(SEQ ID NO: 5)
```
  1 MDFFRVVENQ QPPATMPLNV SFTNRNYDLD YDSVQPYFYC DEEENFYQQQ QQSELQPPAP

61 SEDIWKKFEL LPTPPLSPSR RSGLCSPSYV AVTPFSLRGD NDGGGGSFST ADQLEMVTEL

121 LGGDMVNQSF ICDPDDETFI KNIIIQDCMW SGFSAAAKLV SEKLASYQAA RKDSGSPNPA

181 RGHSVCSTSS LYLQDLSAAA SECIDPSVVF PYPLNDSSSP KSCASQDSSA FSPSSDSLLS

241 STESSPQGSP EPLVLHEETP PTTSSDSEEE QEDEEEIDVV SVEKRQAPGK RSESGSPSAG

301 GHSKPPHSPL VLKRCHVSTH QHNYAAPPST RKDYPAAKRV KLDSVRVLRQ ISNNRKCTSP

361 RSSDTEENVK RRTHNVLERQ RRNELKRSFF ALRDQIPELE NNEKAPKVVI LKKATAYILS

421 VQAEEQKLIS EEDLLRKRRE QLKHKLEQLR NSCA
```

The term "Myc", as used herein, refers to a family of transcription factors which includes c-Myc, N-Myc and L-Myc. Myc protein activates expression of many genes through binding on consensus sequence CACGTG (Enhancer Box sequences or E-boxes) and recruiting histone acetyl-transferases or HATs. However, Myc can also act as a transcriptional repressor. By binding the Miz-1 transcription factor and displacing p300 co-activator, it inhibits expression of Miz-1 target genes. Myc also has a direct role in the control of DNA replication.

The Myc b-HLH-LZ or Myc basic region helix-loop-helix leucine zipper domain refers to a region which determines Myc dimerization with Max protein and binding to Myc-target genes. This region corresponds to amino acids 365-454 of human Myc and is characterized by two alpha helices connected by a loop (Nair, S. K., & Burley, S. K., 2003, Cell, 112: 193-205).

In a preferred embodiment, the polypeptide comprising the polypeptide of SEQ ID NO: 1 comprises, consists of or consists essentially of the SEQ ID NO: 3 shown below.

(SEQ ID NO: 3)
MTEENVKRRTHNVLERQRRNELKRSFFALRDQIPELENNEKAPKVVILKK

ATAYILSVQAETQKLISEIDLLRKQNEQLKHKLEQLRNSXA

In this context, "consisting essentially of" means that the specified molecule would not contain any additional sequences that would alter the activity of SEQ ID NO: 3.

The invention refers to a polypeptide comprising, consisting of or consisting essentially of SEQ ID NO: 1 wherein the residue X at position 89 of SEQ ID NO: 1 is not a cysteine. Said polypeptide can derive from the bHLHZip domain of any Myc protein known in the art, provided that the mutations which result in the tumor suppressor effect are preserved. Thus, the polypeptide that can be used in the present invention may derive from any mammal species, including but not being limited to domestic and farm animals (cows, horses, pigs, sheep, goats, dog, cats or rodents), primates and humans. Preferably, the polypeptide of the invention is derived from human Myc protein (accession number NP_002458, release of Mar. 15, 2015).

In a preferred embodiment, the invention relates to a polypeptide consisting of the polypeptide of SEQ ID NO: 1 wherein the residue X at position 89 of SEQ ID NO: 1 is not a cysteine, or a functionally equivalent variant of said polypeptide.

According to the present invention, the residue at position 89 of SEQ ID NO: 1 may be any amino acid except cysteine.

"Cysteine", as used herein, relates to an amino acid with the formula HO2CCH(NH2)CH2SH. It is encoded by the codons UGU and UGC. The term also includes non-natural cysteine Cysteine can form disulphide bonds in the homodimeric form of Omomyc, hence its mutation for any other amino acid will result in the incapacity of disulfide bond formation and should lead to the same efficacy properties as obtained whit OmoCS. Therefore, the residue at position 89 of SEQ ID NO: 1 may be any natural, non-natural or synthetic amino acid except cysteine, and particularly any amino acid that could not be crosslinked with other monomer of the polypeptide of the invention to form a homodimer.

The term "amino acid" or "residue" refers to naturally occurring and synthetic amino acids, as well as amino acid analogs and amino acid mimetics that function in a manner similar to the naturally occurring amino acids. Amino acids may be referred to herein by either their commonly known three letter symbols or by the one-letter symbols recommended by the IUPAC-IUB Biochemical Nomenclature Commission.

The term amino acid includes naturally occurring amino acids (Ala, Arg, Asn, Asp, Gln, Glu, Gly, His, Ile, Leu, Lys, Met, Phe, Pro, Ser, Thr, Trp, Tyr, Val), uncommon natural amino acids and non-natural (synthetic) amino acids. The amino acids are preferably in the L configuration, but also D configuration, or mixtures of amino acids in the D and L configurations are considered.

The term "natural amino acids" comprises aliphatic amino acids (glycine, alanine, valine, leucine and isoleucine), hydroxylated amino acids (serine and threonine), sulfured amino acids (methionine), dicarboxylic amino acids and their amides (aspartic acid, asparagine, glutamic acid and glutamine), amino acids having two basic groups (lysine, arginine and histidine), aromatic amino acids (phenylalanine, tyrosine and tryptophan) and cyclic amino acids (proline). In an embodiment the residue X at position 89 of SEQ ID NO: 1 is an aliphatic amino acid. In another embodiment the residue X at position 89 of SEQ ID NO: 1 is a sulfured amino acid. In another embodiment the residue X at position 89 of SEQ ID NO: 1 is a dicarboxylic amino acid or their amides. In another embodiment the residue X at position 89 of SEQ ID NO: 1 is an amino acid having two basic groups. In another embodiment the residue X at position 89 of SEQ ID NO: 1 is an aromatic amino acid. In another embodiment the residue X at position 89 of SEQ ID NO: 1 is a cyclic amino acid. In a preferred embodiment the residue X at position 89 of SEQ ID NO: 1 is a hydroxylated amino acid, preferably serine. In a preferred embodiment, the residue X at position 89 of SEQ ID NO: 1 is an amino acid selected from serine, threonine and alanine, preferably selected from serine and alanine.

As used herein, the term "non-natural amino acid" refers to a carboxylic acid, or a derivative thereof, substituted with an amine group and being structurally related to a natural amino acid. Illustrative, non-limiting examples of modified or uncommon amino acids include 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxy lysine, alio hydroxy lysine, 3-hydroxyproline, 4-hydroxyproline, isodesmosine, alloisoleucine, N-methylglycine, N-methyliso leucine, 6-N-methyl-lysine, N-methylvaline, norvaline, norleucine, ornithine, etc.

Illustrative, non-limitative examples of uncommon amino acids are Hydroxylysine and hydroxyproline, Thyroxine, N-methyl arginine and n-acetyl lysine In a preferred embodiment, the residue X at position 89 is any other amino acid that could not be cross-linked with the other monomer of the polypeptide of the invention to form a homodimeric pair.

In a more preferred embodiment of the polypeptide of the invention, the residue at position 89 of SEQ ID NO: 1 is the amino acid serine.

"Serine", as used herein, relates to 2-Amino-3-hydroxypropanoic acid encoded in humans by the codons UCU, UCC, UCA, UCG, AGU and AGC. The term also includes modified serines such as phosphorylated or sulfonated serine, by way of illustrative non-limitative example N-Benzoyl-(2R,3S)-3-phenylisoserine, D-cycloserine, L-isoserine, phenylserine, In a preferred embodiment, the polypeptide of the invention comprises the sequence shown in SEQ ID NO: 2.

```
                                            (SEQ ID NO: 2)
TEENVKRRTHNVLERQRRNELKRSFFALRDQIPELENNEKAPKVVILKKA

TAYILSVQAETQKLISEIDLLRKQNEQLKHKLEQLRNSSA
```

In another preferred embodiment, the polypeptide of the invention consists or consists essentially of SEQ ID NO: 4.

```
                                            (SEQ ID NO: 4)
MTEENVKRRTHNVLERQRRNELKRSFFALRDQIPELENNEKAPKVVILKK

ATAYILSVQAETQKLISEIDLLRKQNEQLKHKLEQLRNSSA
```

In a more preferred embodiment of the polypeptide of the invention, the residue at position 89 of SEQ ID NO: 1 is the amino acid alanine.

"Alanine", as used herein, relates to 2-Aminopropanoic acid encoded in humans by the codons GCU, GCC, GCA, and GCG. The term also includes modified alanines such as N-acetyl-L-alanine.

In a preferred embodiment, the polypeptide of the invention comprises the sequence shown in SEQ ID NO: 63.

```
                                            (SEQ ID NO: 63)
TEENVKRRTHNVLERQRRNELKRSFFALRDQIPELENNEKAPKVVILKKA

TAYILSVQAETQKLISEIDLLRKQNEQLKHKLEQLRNSAA
```

In another preferred embodiment, the polypeptide of the invention consists or consists essentially of SEQ ID NO: 64.

(SEQ ID NO: 64)
MTEENVKRRTHNVLERQRRNELKRSFFALRDQIPELENNEKAPKVVILKK

ATAYILSVQAETQKLISEIDLLRKQNEQLKHKLEQLRNSAA

The term "functionally equivalent variant", when referring to the SEQ ID NO: 1 wherein the residue X at position 89 of SEQ ID NO: 1 is not a cysteine, refers to any polypeptide which results from the deletion, insertion or addition of one or more amino acids with respect to the polypeptide of SEQ ID NO: 1 or which results from the chemical modification of the polypeptide of SEQ ID NO: 1 and which substantially preserves the tumor suppressor activity of the SEQ ID NO: 1 wherein the residue X at position 89 of SEQ ID NO: 1 is not a cysteine, preferably which substantially preserves the tumor suppressor activity of OmoCS. The skilled person will understand that the preservation of the tumor suppressor activity requires that the variant can dimerize with Myc and/or its obligate partner p21/p22Max and inhibit Myc activity once found in the nucleus, that it is capable of translocating across the cell membrane and that it is capable of translocating across the nuclear envelope. In some embodiments, the functionally equivalent variant of the polypeptide of the invention homodimerizes less than Omomyc, or is not forced into homodimers by the formation of disulphide bridge. In particular the disulphide bridge formation in the homodimer form of the polypeptide of the invention is less than in the polypeptide OmoMyc.

"Less homodimerization", as used herein relates to the lower ability of forming obligate homodimers of the polypeptide of the invention even in reducing conditions. In a preferred embodiment, the ability is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% less than the ability of forming homodimers of Omomyc. Reducing conditions, as used herein relates to the presence of a reducing agent, a compound that donates an electron to another chemical species in a redox chemical reaction. Illustrative, non-limitative examples of reducing agents are DTT (dithiothreitol), b-mercaptoethanol or TCEP (tris(2-carboxyethyl)phosphine). It is possible that the amount of homodimers is the same in vitro, and that the difference between the polyopeptide of the invention and Omomyc is present only in cells in presence of heterodimerization partners where the absence of the disulfide enables a potentially higher formation of heterodimers.

Several assays may be used to determine the homodimerization of a peptide, by way of illustrative non-limitative example by thermal denaturation monitored by Circular dichroism, so dimerization may be detected through folding and thermal stability quantification.

Suitable functionally equivalent variants include polypeptides consisting essentially of the polypeptide of SEQ ID NO: 1 wherein the residue X at position 89 of SEQ ID NO: 1 is not a cysteine.

In this context, "consisting essentially of" means that the specified molecule would not contain any additional sequences that would alter the activity of the SEQ ID NO: 1 wherein the residue X at position 89 of SEQ ID NO: 1 is not a cysteine. Suitable functional variants of the targeting peptide are those showing a degree of identity with respect to the peptide of SEQ ID NO:1 (preferably to OmoCS, SEQ ID NO: 4) of about greater than 25% amino acid sequence identity, such as 25%, 30%, 40%, 50%, 60%, 65%, 70%, 75%, 80%, 85%, 90%, 91%, 92%, 93%, 94%, 95%, 96%, 97%, 98% or 99%. The degree of identity between two polypeptides is determined using computer algorithms and methods that are widely known for the persons skilled in the art. The identity between two amino acid sequences is preferably determined by using the BLASTP algorithm as described previously [BLAST Manual, Altschul, S., et al., NCBI NLM NIH Bethesda, Md. 20894, Altschul, S., et al., J. Mol. Biol. 1990; 215: 403-410]. In a preferred embodiment, the sequence identity is determined throughout the whole length of the polypeptide of SEQ ID NO: 1 or throughout the whole length of the variant or of both.

The functionally equivalent variants of the polypeptide of the invention may also include post-translational modifications, such as glycosylation, acetylation, isoprenylation, myristoylation, proteolytic processing, etc.

Alternatively, suitable functional variants of the targeting peptide are those wherein one or more positions within the polypeptide of the invention contain an amino acid which is a conservative substitution of the amino acid present in the protein mentioned above. "Conservative amino acid substitutions" result from replacing one amino acid with another having similar structural and/or chemical properties. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Selection of such conservative amino acid substitutions is within the skill of one of ordinary skill in the art and is described, for example, by Dordo et al., (J. Mol. Biol, 1999, 217; 721-739) and Taylor et al., (J. Theor. Biol., 1986, 119:205-218).

In a preferred embodiment, the whole sequence of the functionally equivalent variant of SEQ ID NO: 1 does not contain a cysteine amino acid. It will be understood that he functionally equivalent variants of the SEQ ID NO: 1 wherein the residue X at position 89 of SEQ ID NO: 1 is not a cysteine contain mutations at positions corresponding to the mutations E61T, E68I, R74Q and R75N found in Omomyc derived from human c-Myc. The position wherein said mutations have to occur in the functionally equivalent variant can be determined by a multiple sequence alignment of different Myc sequences and identified by the alignment of those positions corresponding to positions 61, 68, 74 and 75 within the sequence of Omomyc derived from human c-Myc.

A multiple sequence alignment is an extension of pairwise alignment to incorporate more than two sequences at a time. Multiple alignment methods align all of the sequences in a given query set. A preferred multiple sequence alignment program (and its algorithm) is ClustalW, Clustal2W or ClustalW XXL (see Thompson et al. (1994) Nucleic Acids Res 22:4673-4680). Once the sequences of c-Myc from different organisms and of the variant are compared (aligned) as described herein, the skilled artisan can readily identify the positions within each of the sequence corresponding to positions E61T, E68I, R74Q and R75N found in Omomyc and introduce within the variant of SEQ ID NO: 1 wherein the residue X at position 89 of SEQ ID NO: 1 is not a cysteine, mutations corresponding to the E61T, E68I, R74Q and R75N mutations found in Omomyc derived from human c-Myc.

Suitable assays for determining whether a polypeptide can be considered as a functionally equivalent variant of SEQ ID NO: 1 wherein the residue X at position 89 of SEQ ID NO: 1 is not a cysteine include, without limitation:

- Assays which measure the capacity of the polypeptide to form dimeric complexes with Max and Myc, such as the assays based on the expression of a reporter gene as described in Soucek et al. (Oncogene, 1998, 17: 2463-2472) as well as PLA (protein Ligation assay) or Co-immunoprecipitation.
- Assays which measure the capacity of the polypeptide to bind to the Myc/Max recognition site within DNA (the CACGTG site), such as the electrophoretic mobility shift assay (EMSA) described in Soucek et al. (supra.).
- Assays which measure the capacity to repress Myc-induced transactivation, such as the assay based on the expression of a reporter gene under the control of the DNA binding sites specific for Myc/Max as described by Soucek et al. (supra.).
- Assays based on the capacity of the gene product or the polypeptide to inhibit growth of cells expressing the myc oncogene, as described by Soucek et al. (supra.).
- Assays which measure the ability of the polypeptide to enhance myc-induced apoptosis, such as the assays described by Soucek et al. (Oncogene, 1998: 17, 2463-2472). Moreover, any assay commonly known in the art for assessing apoptosis in a cell can be used, such as the Hoechst staining, Propidium Iodide (PI) or Annexin V staining, trypan blue, DNA laddering/fragmentation and TUNEL.

In a preferred embodiment, a functionally equivalent variant of SEQ ID NO: 1 wherein the residue X at position 89 of SEQ ID NO: 1 is not a cysteine include those sequences having one or more, preferably all the following features: ability to dimerize with Myc and inhibiting its activity, translocation across the cell membrane, translocation to the nucleus, inability to form homodimers or reduced capacity to form homodimers compared to Omomyc, a cell viability in an in vitro assay as performed in Example 1 lower than Omomyc at an amount of 12.5 nM mRNA encoding the polypeptide of the invention. In a preferred embodiment, the functionally equivalent variant of the invention corresponds to a sequence that mediates a cell viability in an in vitro assay as performed in Example 1 lower than Omomyc at an amount of 12.5 nM mRNA encoding the polypeptide of the invention.

In a preferred embodiment, a polypeptide is considered a functionally equivalent variant of SEQ ID NO: 1 wherein the residue X at position 89 of SEQ ID NO: 1 is not a cysteine if it shows an activity in one or more of the above assays which is at least 10%, 20%, 30%, 40%, 50%, 60%, 70%, 80%, 90% or 100% of the activity of SEQ ID NO: 1 wherein the residue X at position 89 of SEQ ID NO: 1 is not a cysteine (preferably of the activity of OmoCS).

Additionally, functionally equivalent variants of SEQ ID NO: 1 wherein the residue X at position 89 of SEQ ID NO: 1 is not a cysteine, are also capable of transducing cells after the variant is contacted with said cell.

In a preferred embodiment, a polypeptide is considered as a functionally equivalent variant of SEQ ID NO: 1 wherein the residue X at position 89 of SEQ ID NO: 1 is not a cysteine if it is capable of transducing a target cell at least 10%, 20%, 30%, 40%, 50%, 60%, 70%, 80%, 90% or 100% as efficiently as SEQ ID NO: 1 wherein the residue X at position 89 of SEQ ID NO: 1 is not a cysteine (preferably as OmoCS, SEQ ID NO: 4).

Additionally, functionally equivalent variants of SEQ ID NO: 1 wherein the residue X at position 89 of SEQ ID NO: 1 is not a cysteine, are also capable of translocating to the nucleus of the target tumor cell.

In a preferred embodiment, a polypeptide is considered as a functionally equivalent variant of SEQ ID NO: 1 wherein the residue X at position 89 of SEQ ID NO: 1 is not a cysteine if it is capable of translocating to the nucleus of the target tumor cells at least 10%, 20%, 30%, 40%, 50%, 60%, 70%, 80%, 90% or 100% as efficiently as the SEQ ID NO: 1 wherein the residue X at position 89 of SEQ ID NO: 1 is not a cysteine (preferably as OmoCS, SEQ ID NO: 4).

Suitable assays for determining whether a polypeptide is a functionally equivalent variant of SEQ ID NO: 1 wherein the residue X at position 89 of SEQ ID NO: 1 is not a cysteine in terms of its ability to translocate across the cellular membrane and to the nucleus include double labelling of a cell with a reagent specific for the polypeptide and with a dye which specifically labels the nucleus of the cell (such as DAPI or Hoechst dye). In a preferred embodiment, the detection of the polypeptide of the invention is performed by confocal microscopy or by fluorescence microscopy.

The polypeptide of the invention of SEQ ID NO: 1 also contains the M2 domain of c-Myc, having the sequence RQRRNELKRSF (SEQ ID NO: 55) (see Dang and Lee, Mol. Cell. Biol., 1988, 8:4048-4054), and which corresponds to a nuclear localization signal.

In another preferred embodiment, the functionally equivalent variant of SEQ ID NO: 1 wherein the residue X at position 89 of SEQ ID NO: 1 is not a cysteine comprises the sequence SEQ ID NO: 55.

The term "nuclear localization signal", as used herein, refers to an amino acid sequence of about 4-20 amino acid residues in length, which serves to direct a protein to the nucleus. Typically, the nuclear localization sequence is rich in basic amino acids and exemplary sequences are well known in the art (Gorlich D. (1998) EMBO 5.17:2721-7).

In some embodiments, the NLS is selected from the group consisting of the SV40 large T Antigen NLS (PKKKRKV, SEQ ID NO: 6); the Nucleoplasmin NLS (KRPAATKK-AGQAKKKK, SEQ ID NO: 7); the CBP80 NLS (RRRHS-DENDGGQPHKRRK, SEQ ID NO: 8); the HIV-I Rev protein NLS (RQARRNRRRWE, SEQ ID NO: 9); the HTLV-I Rex (MPKTRRRPRRSQRKRPPT, SEQ ID NO: 10); the hnRNP A NLS (NQSSNFGPMKGGNFG-GRSSGPYGGGGQYFKPRNQGGY, SEQ ID NO: 11); the rpL23a NLS (VHSHKKKKIRT-SPTFTTPKTLRLRRQPKYPRKSAPRRNKLDHY, SEQ ID NO: 12). In one embodiment of the invention, the nuclear localization signal comprises the motif K (K/R) X (K/R) (SEQ ID NO: 13).

Additionally, functionally equivalent variants of SEQ ID NO: 1 wherein the residue X at position 89 of SEQ ID NO: 1 is not a cysteine are also capable of reaching the nuclei of the transduced cells after the variant is contacted with said cell. It will be understood that functionally equivalent variants of SEQ ID NO: 1 wherein the residue X at position 89 of SEQ ID NO: 1 is not a cysteine contain the NLS found in SEQ ID NO: 1 wherein the residue X at position 89 of SEQ ID NO: 1 is not a cysteine or another functional NLS. In another embodiment the polypeptide of the invention does not contain the native NLS found in SEQ ID NO: 1 and contains another functional NLS replacing said NLS found in SEQ ID NO: 1 or in any other part of the polypeptide of the invention.

Conjugate of the Invention

In another aspect, the invention relates to a conjugate comprising:
 a) the polypeptide or functionally equivalent variant of said polypeptide according to the invention and
 b) a chemical moiety that facilitates cellular uptake of the polypeptide or of the functionally equivalent variant of said polypeptide.

The term "conjugate", as used herein, refers to two or more compounds which are covalently linked together so that the function of each compound is retained in the conjugate.

In preferred embodiments, the conjugates according to the invention comprise at least 1, at least 2, at least 3, at least 4, at least 5, at least 6, at least 7, at least 8, at least 9, at least 10 or more chemical moieties that facilitate cellular uptake of the polypeptide or of the functionally equivalent variant of said polypeptide.

In one embodiment, the chemical moiety that facilitates cellular uptake of the polypeptide is a lipid or a fatty acid.

A fatty acid generally is a molecule comprising a carbon chain with an acidic moiety (e.g., carboxylic acid) at an end of the chain. The carbon chain of a fatty acid may be of any length, however, it is preferred that the length of the carbon chain be of at least 2, 3, 4, 5, 6, 7, 8, 9, 10, 11, 12, 13, 14, 15, 16, 17, 18, 19, 20 or more carbon atoms, and any range derivable therein. In certain embodiments, the length of the carbon chain is from 4 to 18 carbon atoms in the chain portion of the fatty acid. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated. The fatty acid may be branched, though in preferable embodiments of the present invention, it is unbranched. Specific fatty acids include, but are not limited to, linoleic acid, oleic acid, palmitic acid, linolenic acid, stearic acid, lauric acid, myristic acid, arachidic acid, palmitoleic acid, arachidonic acid.

In a preferred embodiment, the chemical moiety that facilitates cellular uptake of the polypeptide is a cell penetrating peptide sequence, in which case, the conjugate is a fusion protein comprising a polypeptide of the invention or the functionally equivalent variant of said polypeptide and the cell penetrating peptide sequence.

The term "fusion protein" relates to proteins generated by gene technology which consist of two or more functional domains derived from different proteins. A fusion protein may be obtained by conventional means, e.g., by means of gene expression of the nucleotide sequence encoding for said fusion protein in a suitable cell. It will be understood that the cell penetrating peptide refers to a cell penetrating peptide which is different from the cell penetrating peptide which forms part of the polypeptide of SEQ ID NO: 1 or of the functionally equivalent variant of said polypeptide.

The term "cell penetrating peptide sequence" is used in the present specification interchangeably with "CPP", "protein transducing domain" or "PTD". It refers to a peptide chain of variable length that directs the transport of a protein inside a cell. The delivering process into cell commonly occurs by endocytosis but the peptide can also be internalized into cell by means of direct membrane translocation. CPPs typically have an amino acid composition that either contains a high relative abundance of positively charged amino acids such as lysine or arginine or has sequences that contain an alternating pattern of polar/charged amino acid and non-polar, hydrophobic amino acids. Examples of CPPs which can be used in the present invention include, without limitation, the CPP found in Drosophila antennapedia protein (RQIKIWFQNRRMKWKK; SEQ ID NO:14), the CPP found in the herpesvirus simplex 1 (HSV-1) VP22 DNA-binding protein (DAATATRGRSAASRPTERPRAPARSASRPRRPVE; SEQ ID NO:15), the CPP of Bac-7 (RRIRPRPPRLPRPRPRPLPFPRPG; SEQ ID NO: 16), the CPPs of the HIV-1 TAT protein consisting of amino acids 49-57 (RKKRRQRRR; SEQ ID NO: 17), amino acids 48-60 (GRKKRRQRRRTPQ; SEQ ID NO: 18), amino acids 47-57 (YGRKKRRQRRR; SEQ ID NO: 19), the CPP of 5413-PV peptide (ALWKTLLKKVLKAPKKKRKV; SEQ ID NO: 20), the CPP of penetratin (RQIKWFQNRRMKWKK; SEQ ID NO: 21), the CPP of SynB1 (RGGRLSYSRRRFSTSTGR; SEQ ID NO: 22), the CPP of SynB3 (RRLSYSRRRF; SEQ ID NO:23), the CPP of PTD-4 (PIRRRKKLRRLK; SEQ ID NO: 24), the CPP of PTD-5 (RRQRRTSKLMKR; SEQ ID NO: 25), the CPP of the FHV Coat-(35-49) (RRRRNRTRRNRRRVR; SEQ ID NO: 26), the CPP of BMV Gag-(7-25) (KMTRAQRRAAARRNRWTAR; SEQ ID NO: 27), the CPP of HTLV-II Rex-(4-16) (TRRQRTRRARRNR; SEQ ID NO:28), the CPP of D-Tat (GRKKRRQRRRPPQ; SEQ ID NO:29), the CPP R9-Tat (GRRRRRRRRRPPQ; SEQ ID NO: 30), the CPP of MAP (KLALKLALKLALALKLA; SEQ ID NO: 31), the CPP of SBP (MGLGLHLLVLAAALQGAWSQPKKKRKV; SEQ ID NO: 32), the CPP of FBP (GALFLGWLGAAGSTMGAWSQPKKKRKV; SEQ ID NO: 33), the CPP of MPG (ac-GALFLGFLGAAGSTMGAWSQPKKKRKV-cya; SEQ ID NO: 34), the CPP of MPG(ENLS) (ac-GALFLGFLGAAGSTMGAWSQPKSKRKV-cya; SEQ ID NO: 35), the CPP of Pep-1 (ac-KETWWETWWTEWSQPKKKRKV-cya; SEQ ID NO: 36), the CPP of Pep-2 (ac-KETWFETWFTEWSQPKKKRKV-cya; SEQ ID NO: 37), a polyarginine sequence having the structure $R_N$ (wherein N is between 4 and 17), the GRKKRRQRRR sequence (SEQ ID NO: 38), the RRRRRRLR sequence (SEQ ID NO: 39), the RRQRRTSKLMKR sequence (SEQ ID NO: 40); Transportan GWTLNSAGYLLGKINLKALAALAKKIL (SEQ ID NO: 41); KALAWEAKLAKALAKALAKHLAKALAKALKCEA (SEQ ID NO: 42); RQIKIWFQNRRMKWKK (SEQ ID NO: 43); the YGRKKRRQRRR sequence (SEQ ID NO: 44); the RKKRRQRR sequence (SEQ ID NO: 45); the YARAAARQARA sequence (SEQ ID NO: 46); the THRLPRRRRRR sequence (SEQ ID NO: 47); the GGRRARRRRRR sequence (SEQ ID NO: 48).

In a preferred embodiment, said cell-penetrating peptide is not the endogenous contained in SEQ ID NO: 1.

In a preferred embodiment the CPP is the CPP of the HIV-1 TAT protein consisting of amino acids 49-57 (RKKRRQRRR, SEQ ID NO: 49). In another preferred embodiment the CPP is the GRKKRRQRRR sequence (SEQ ID NO: 50) or RRRRRRRR (SEQ ID NO: 51).

In one embodiment, the cell-penetrating peptide sequence is fused at the N-terminus of the polypeptide of the invention or of the functionally equivalent variant of said polypeptide. In another embodiment, the cell-penetrating peptide is fused at the C-terminus of the polypeptide of the invention or of the functionally equivalent variant of said polypeptide.

In preferred embodiments, the conjugates or fusion proteins according to the invention comprise, in addition to the own cell penetrating peptide found in the polypeptide of SEQ ID NO: 1 or of the functionally equivalent variant of said polypeptide, at least 1, at least 2, at least 3, at least 4, at least 5, at least 6, at least 7, at least 8, at least 9, at least 10 or more additional cell penetrating peptides.

Suitable fusion proteins of the invention include the polypeptides OmoCS*TAT and OmoCS*LZArg as defined below:

| Name | SEQ ID NO: | Sequence |
|---|---|---|
| OmoCS*TAT | 52 | MTEENVKRRTHNVLERQRRNELKRSFFALRDQIP ELENNEKAPKVVILKKATAYILSVQAETQKLISE IDLLRKQNEQLKHKLEQLRNSSAGRKKRRQRRR |
| OmoCS*LZArg | 53 | MTEENVKRRTHNVLERQRRNELKRSFFALRDQIP ELENNEKAPKVVILKKATAYILSVQAETQKLISE IDLLRKQNEQLKHKLEQLRNSSARRRRRRRR |

In another preferred embodiment, the conjugates or fusion proteins of the invention comprise the polypeptide of the invention or a functionally equivalent variant thereof and further comprise an N-terminal or C-terminal nuclear localization signal.

The skilled person will understand that it may be desirable that the fusion protein further comprises one or more flexible peptides that connect the polypeptide of the invention or the functionally equivalent variant of said polypeptide, the cell penetrating peptide sequence and/or the NLS. Thus, in a particular embodiment the polypeptide of the invention is directly connected to the cell penetrating peptide sequence. In another particular embodiment, the polypeptide of the invention is connected to the cell penetrating peptide sequence through a flexible peptide. In an embodiment the polypeptide of the invention is directly connected to the NLS. In another embodiment the polypeptide of the invention is connected to the NLS through flexible peptide.

In a particular embodiment the polypeptide of the invention is directly connected to the cell penetrating peptide sequence and to the NLS.

In one embodiment, the NLS is one of the NLS which appears endogenously in the Myc sequence, such as the M1 peptide (PAAKRVKLD, SEQ ID NO: 54) or the M2 peptide (RQRRNELKRSF, SEQ ID NO: 55).

In another embodiment the additional NLS refers to an NLS which is different to the endogenous NLS found in polypeptide of SEQ ID NO: 1 or in the functionally equivalent variant of said polypeptide.

In preferred embodiments, the conjugates or fusion proteins according to the invention comprise, in addition to the endogenous NLS found in the polypeptide of the invention or in the functionally equivalent variant thereof, at least 1, at least 2, at least 3, at least 4, at least 5, at least 6, at least 7, at least 8, at least 9, at least 10 NLS.

In another particular embodiment, the polypeptide of the invention is connected to the cell penetrating peptide sequence through a first flexible peptide linker and to the NLS through a second flexible peptide linker.

As used herein, the term "flexible peptide", "spacer peptide" or "linker peptide" refers to a peptide that covalently binds two proteins or moieties but which is not part of either polypeptide, allowing movement of one with respect to the other, without causing a substantial detrimental effect on the function of either the protein or the moiety. Thus, the flexible linker does not affect the tumour suppressor activity of the polypeptide sequence, the cell penetrating activity of the cell penetrating peptide or the nuclear localization capacity of the NLS.

The flexible peptide comprises at least one amino acid, at least two amino acids, at least three amino acids, at least four amino acids, at least five amino acids, at least six amino acids, at least seven amino acids, at least eight amino acids, at least nine amino acids, at least 10 amino acids, at least 12 amino acids, at least 14 amino acids, at least 16 amino acids, at least 18 amino acids, at least 20 amino acids, at least 25 amino acids, at least 30 amino acids, at least 35 amino acids, at least 40 amino acids, at least 45 amino acids, at least 50 amino acids, at least 60 amino acids, at least 70 amino acids, at least 80 amino acids, at least 90 amino acids, or about 100 amino acids. In some embodiments the flexible peptide will permit the movement of one protein with respect to the other in order to increase solubility of the protein and/or to improve its activity. Suitable linker regions include a polyglycine region, the GPRRRR sequence (SEQ ID NO: 56) of combinations of glycine, proline and alanine residues.

In some embodiments the fusion protein of the invention can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, the heterologous polypeptide can comprise one or more chemically reactive groups including, among others, ketone, aldehyde, Cys residues and Lys residues.

In a particular embodiment, the conjugates or fusion proteins of the invention comprise a tag bound to the conjugate or to the C-terminal or N-terminal domain of said fusion protein or variant of said polypeptide. Said tag is generally a peptide or amino acid sequence which can be used in the isolation or purification of said fusion protein. Thus, said tag is capable of binding to one or more ligands, for example, one or more ligands of an affinity matrix such as a chromatography support or bead with high affinity. An example of said tag is a histidine tag (His-tag or HT), such as a tag comprising 6 residues of histidine (His6 or H6), which can bind to a column of nickel (Ni2+) or cobalt (Co2+) with high affinity. His-tag has the desirable feature that it can bind its ligands under conditions that are denaturing to most proteins and disruptive to most protein-protein interactions. Thus, it can be used to remove the bait protein tagged with H6 following the disruption of protein-protein interactions with which the bait has participated.

Additional illustrative, non-limitative, examples of tags useful for isolating or purifying a fusion protein include Arg-tag, FLAG-tag (DYKDDDDK; SEQ ID NO: 57), Strep-tag (WSHPQFEK; SEQ ID NO: 58), an epitope capable of being recognized by an antibody, such as c-myc-tag (recognized by an anti-c-myc antibody), HA tag (YPYDVPDYA; SEQ ID NO: 59), V5 tag (GKPIPNPLLGLDST; SEQ ID NO: 60), SBP-tag, S-tag, calmodulin binding peptide, cellulose binding domain, chitin binding domain, glutathione S-transferase-tag, maltose binding protein, NusA, TrxA, DsbA, Avi-tag, etc. (Terpe K., Appl. Microbiol. Biotechnol. 2003, 60:523-525), an amino acid sequence such as AHGHRP (SEQ ID NO: 61) or PIHDHDHPHLVIHSGMTCXXC (SEQ ID NO: 62), β-galactosidase and the like.

The tag can be used, if desired, for the isolation or purification of said fusion protein.

Polynucleotide, Vector and Host Cell of the Invention

In another aspect, the invention relates to a polynucleotide encoding a polypeptide according to the invention or a conjugate according to the invention.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules. As used herein, mRNA refers to an RNA that can be translated in a cell.

In preferred embodiment, the polynucleotide of the invention is an mRNA. mRNA can be chemically synthesized, can be obtained by means of in vitro transcription or can be synthesized in vivo in the target cell. The nucleotide sequences that form the polynucleotide encoding the conjugate or fusion protein of the invention are in the same correct reading frame for expression thereof.

In another aspect, the invention relates to a vector comprising a polynucleotide of the invention.

The term "vector", as used herein, refers to a nucleic acid sequence comprising the necessary sequences so that after transcribing and translating said sequences in a cell a polypeptide encoded by the polynucleotide of the invention is generated. Said sequence is operably linked to additional segments that provide for its autonomous replication in a host cell of interest. Preferably, the vector is an expression vector, which is defined as a vector which, in addition to the regions of the autonomous replication in a host cell, contains regions operably linked to the nucleic acid of the invention and which are capable of enhancing the expression of the products of the nucleic acid according to the invention. The vectors of the invention can be obtained by means of techniques widely known in the art.

Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Suitable vectors comprising a polynucleotide of the invention are vectors derived from expression vectors in prokaryotes such as pUC18, pUC19, pBluescript and their derivatives, mp18, mp19, pBR322, pMB9, ColEI, pCR1, RP4, phages and "shuttle" vectors such as pSA3 and pAT28, expression vectors in yeasts such as vectors of the 2-micron plasmid type, integration plasmids, YEP vectors, centromeric plasmids and similar, expression vectors in insect cells such as the vectors of the pAC series and of the pVL series, expression vectors in plants such as vectors of the series pIBI, pEarleyGate, pAVA, pCAMBIA, pGSA, pGWB, pMDC, pMY, pORE and similar and expression vectors in superior eukaryote cells based on viral vectors (adenovirus, virus associated to adenovirus as well as retrovirus and, in particular, lentivirus) as well as non-viral vectors such as pSilencer 4.1-CMV (Ambion), pcDNA3, pcDNA3.1/hyg, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL, pKSV-10, pBPV-1, pML2d and pTDT1. In a preferred embodiment, the polynucleotide of the invention is comprised in a vector selected from the group consisting of pEGFP or pBabe retroviral vectors and pTRIPZ or pSLIK lentiviral vectors.

The vector of the invention may be used to transform, transfect or infect cells that can be transformed, transfected or infected by said vector. Said cells may be prokaryotic or eukaryotic.

The vector preferably comprises the polynucleotide of the invention operationally bound to sequences that regulate the expression of the polynucleotide of the invention. The regulatory sequences of use in the present invention may be nuclear promoters or, alternatively, enhancer sequences and/or other regulatory sequences that increase expression of the heterologous nucleic acid sequence. In principle, any promoter can be used in the present invention provided said promoter is compatible with the cells wherein the polynucleotide is to be expressed. Thus, promoters suitable for realizing the present invention include, but are not necessarily limited to, constitutive promoters such as derivatives of eukaryotic virus genomes such as polyoma virus, adenovirus, SV40, CMV, avian sarcoma virus, hepatitis B virus, the metallothionein gene promoter, the herpes simplex virus thymidine kinase gene promoter, LTR regions of retroviruses, the immunoglobulin gene promoter, the actin gene promoter, the EF-1alpha gene promoter as well as inducible promoters wherein protein expression depends on the addition of a molecule or exogenous signal, such as tetracycline systems, the NFκB/UV light system, the Cre/Lox system and the heat shock genes promoter, the regulable RNA polymerase II promoters described in WO/2006/135436 and tissue-specific promoters.

In another aspect, the invention relates to a host cell comprising a polypeptide of the invention, a conjugate of the invention, a polynucleotide of the invention or a vector of the invention.

Cells suitable in the present invention include, but are not limited to, mammalian, plant, insect, fungal and bacterial cells. Bacterial cells include, but are not limited to, cells from Gram-positive bacteria such as species from the genera *Bacillus, Streptomyces* and *Staphylococcus* and cells from Gram-negative bacteria such as cells from the genera *Escherichia* and *Pseudomonas*. Fungal cells preferably include yeast cells such as *Saccharomyces, Pichia pastoris* and *Hansenula* polymorphs. Insect cells include, but are not limited to, *Drosophila* cells and Sf9 cells. Plant cells include, amongst others, crop plant cells such as cereals, medicinal or ornamental plants or from bulbs. Mammalian cells suitable for the present invention include epithelial cell lines (porcine, etc.), osteosarcoma cell lines (human, etc.), neuroblastoma cell lines (human, etc.), epithelial carcinomas (human, etc.), glial cells (murine, etc.), hepatic cell lines (from monkey, etc.), CHO (Chinese Hamster Ovary) cells, COS cells, BHK cells, HeLa, 911, AT1080, A549, 293 or PER.C6 cells, human NTERA-2 ECC cells, D3 cells from the mESC line, non-human embryonic stem cells, NIH3T3, 293T, REH and MCF-7 cells and hMSC cells.

All the terms and embodiments previously described are equally applicable to this aspect of the invention.

Pharmaceutical Composition of the Invention

In another aspect, the invention relates to a pharmaceutical composition comprising a pharmaceutically effective amount of a polypeptide or functional equivalent variant of said polypeptide according to the invention, a conjugate according to the invention, a polynucleotide according to the invention, a vector according to the invention or a host cell according to the invention and a pharmaceutically acceptable excipient.

As it is used in the present invention, the expression "pharmaceutical composition" relates to a formulation that has been adapted for administering a predetermined dose of one or several therapeutic useful agents to a cell, a group of cells, an organ, a tissue or an animal in which cell division is uncontrolled, such as cancer.

The expression "pharmaceutical effective amount", as used herein, is understood as an amount capable of providing a therapeutic effect, and which can be determined by the person skilled in the art by commonly used means. The amount of the polypeptide of the invention or of the functionally equivalent variant thereof, the conjugate, the polynucleotide, the vector or of the host cell of the invention or of the antitumoral compound that may be combined in the pharmaceutical compositions according to the invention will vary depending upon the subject and the particular mode of administration. Those skilled in the art will appreciate that dosages may also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

The appropriate dosage of the active principle or principles within the pharmaceutical composition will depend on the type of cancer to be treated, the severity and course of the disease, whether the composition is administered for preventive or therapeutic purposes, previous therapy, the patient's clinical history and response to the peptide or polypeptide, and the discretion of the attending physician. The amount of the polypeptide of the invention or of the functionally equivalent variant thereof, the conjugate, the polynucleotide, the vector or of the host cell of the invention is suitably administered to the patient at one time or over a series of treatments. Depending on the type and severity of the disease, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The pharmaceutical compositions of the invention also contain one or several additional pharmaceutically acceptable excipients. "Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability. The excipient or carrier also includes any substance that serves to improve the delivery and the effectiveness of the active principle within the pharmaceutical composition. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the fusion protein or of the compositions forming part of the pharmaceutical compositions. Examples of proper carriers are well known in the literature (see for example Remington's Pharmaceutical Sciences, 19th ed., Mack Publishing Company, Easton, Pa., 1995). Examples of carriers without limitation are a series of saccharide such as lactose, dextrose, sucrose, sorbitol, mannitol, xylitol, erythritol, and maltitol; a series of starch such as corn starch, wheat starch, rice starch, and potato starch; a series of cellulose such as cellulose, methyl cellulose, sodium carboxy methyl cellulose, and hydroxyl propylmethyl cellulose; and a series of filler such as gelatin and polyvinyl pyrrolidone. In some cases, a disintegrant such as cross-linked polyvinyl pyrrolidone, agar, alginic acid, or sodium alginate may be added.

The number and the nature of the pharmaceutically acceptable excipients depend on the desired dosage form. The pharmaceutically acceptable excipients are known by the person skilled in the art (Fauli y Trillo C. (1993) "Tratado de Farmacia Galénica", Luzán 5, S.A. Ediciones, Madrid). Said compositions can be prepared by means of the conventional methods known in the state of the art ("Remington: The Science and Practice of Pharmacy", $20^{th}$ edition (2003) Genaro A. R., ed., Lippincott Williams & Wilkins, Philadelphia, US).

For pharmaceutical compositions comprising an agent that is a nucleic acid molecule, the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., Science 259:1745-49, 1993 and reviewed by Cohen, Science 259:1691-1692, 1993. The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., Trends Cell Bio. 2:139 (1992); Delivery Strategies for Antisense Oligonucleotide Therapeutics, ed. Akhtar, 1995, Maurer et al., Mol. Membr. Biol. 16:129-40 (1999); Hofland and Huang, Handb. Exp. Pharmacol. 137:165-92 (1999); Lee et al., ACS Symp. Ser. 752:184-92 (2000); U.S. Pat. No. 6,395,713; International Patent Application Publication No. WO 94/02595); Selbo et al., Int. J. Cancer 87:853-59 (2000); Selbo et al., Tumour Biol. 23:103-12 (2002); U.S. Patent Application Publication Nos. 2001/0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., Bioconjug. Chem. 10: 1068-74 (1999); Wang et al., International Application Publication Nos. WO 03/47518 and WO 03/46185); poly(lactic-co-glycolic)acid (PLGA) and PLCA microspheres (also useful for delivery of peptides and polypeptides and other substances) (see, e.g., U.S. Pat. No. 6,447,796; U.S. Patent Application Publication No. 2002/130430); biodegradable nanocapsules; and bioadhesive microspheres, or by proteinaceous vectors (International Application Publication No. WO 00/53722). In another embodiment, the nucleic acid molecules for use in altering (suppressing or enhancing) an immune response in an immune cell and for treating an immunological disease or disorder can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/0077829).

In a preferred embodiment, the pharmaceutical composition or pharmaceutical combination according to the invention further comprises together or separately an antitumoral agent.

As used herein, "antitumoral agent" is understood as said biological or chemical compound which treats tumors or prevents the formation thereof. In a preferred embodiment said antitumoral agent is selected from the group consisting of a cytotoxic agent, an antiangiogenic agent, an antimetastatic agent and an antiproliferative agent.

As used in the present invention, the term "cytotoxic agent" relates to an agent which is capable of promoting cell death and which has capacity for reducing the growth, stopping the growth or destroying cells and, particularly, rapidly proliferating cells and, yet more particularly, tumor cells. Cell death can be caused by any mechanism, such as for example apoptosis, although it is not limited to this cause, by the metabolism inhibition, the interference with the organization of the cytoskeleton or the chemical modification of the DNA. The term cytotoxic agent comprises any chemotherapy agent including small organic molecules, peptides, oligonucleotides and the like; toxins; enzymes; cytokines; radioisotopes or radiotherapy agents.

"Antiangiogenic agent" is understood as a chemical or biological substance which inhibits or reduces the formation of new blood vessels, i.e., angiogenesis.

Antiangiogenic agents that can be used with the polypeptide according to the first aspect of the invention or with the fusion protein according to the second aspect of the invention include, without limitation, an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAI, interleukin 12, IM862, amiloride, angiostatin, K1-3 angiostatin, K1-5 angiostatin, Captopril, DL-alpha-difluoromethylornithine, DL-alpha-difluoromethylornithine HCl, endostatin, fumagillin, herbimycin A, 4-Hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide.

"Antimetastatic agent" is understood as a chemical or biological substance which inhibits or reduces metastasis, i.e., the distance propagation, fundamentally by the lymphatic or blood stream, of the cancer causing cells, and the growth of new tumors in the destination sites of said metastasis.

"Antiproliferative agent" is understood as a chemical or biological substance which is capable of preventing or inhibiting the formation or growth of tumors. Antiproliferative agents include but are not limited to (i) antimetabolites such as folic acid antimetabolites (aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine) (ii) natural products, such as antitumor antibiotics and mitotic inhibitors such as *vinca* alkaloids such as vindesine, vincristine, vinblastine, vinorelbine; taxanes such as paclitaxel (Taxol™), docetaxel (Taxotere™); colchicine (NSC 757), thiocolchicine (NSC 361792), colchicine derivatives (e. g., NSC 33410), and allocolchicine (NSC 406042); halichondrin B (NSC 609395); dolastatin 10 (NSC 376128); maytansine (NSC 153858); rhizoxin (NSC 332598); epothilone A, epothilone B; discodermolide; estramustine; nocodazole; (iii) hormones and antagonists thereof such as tamoxifen, toremifene, anastrozole, arzoxifene, lasofoxifene, raloxifene, nafoxidine, fulvestrant, aminoglutethimide, testolactone, atamestane, exemestane, fadrozole, formestane, letrozole, goserelin, leuprorelin or leuprolide, buserelin, histrelin, megestrol and fluoxymesterone; (iv) biological agents, such as viral vectors, interferon alpha and interleukines; (v) platinum based compounds such as carboplatin, cisplatin [cis-diamminedichloroplatinum, (CDDP)], oxaliplatin, iproplatin, nedaplatin, triplatin tetranitrate, tetraplatin, satraplatin (JM216), JM118 [cis ammine dichloro (II)], JM149 [cis ammine dichloro (cyclohexylamine) trans dihydroxo platinum (IV)], JM335 [trans ammine dichloro dihydroxo platinum (IV)], transplatin, ZD0473, cis, trans, cis-Pt(NH3)(C6H11NH2)(OOCC3H7) 2C1, malanate-1,2-diaminociclohexanoplatin(II), 5-sulphosalycilate-trans-(1,2-diaminociclohexane)platin (II) (SSP), poly-[(trans-1,2-diaminocyclohexane)platin]-carboxyamilose (POLY-PLAT) and 4-hydroxy-sulphonylphenylacetate (trans-1,2-diaminocyclohexane) platinum (II) (SAP) and the like and (vi) DNA-alkylating drugs such as nitrogen mustards, nitrosoureas, ethylenimine derivatives, alkyl sulfonates and triazenes, including, but not limited to, cyclophosphamide (Cytoxan™), busulfan, improsulfan, piposulfan, pipobroman, melphalan (L-sarcolysin), chlorambucil, mechlorethamine or mustine, uramustine or uracil mustard, novembichin, phenesterine, trofosfamide, Ifosfamide, carmustine (BCNU), lomustine (CCNU), chlorozotocin, fotemustine, nimustine, ranimnustine, semustine (methyl-CCNU), streptozocin, thiotepa, triethylenemelamine, triethylenethiophosphoramine, procarbazine, altretamine, dacarbazine, mitozolomide and temozolomide.

In the case of the pharmaceutical compositions or combinations according to the invention that contain an antitumoral agent, the composition may be presented as a single formulation (for example, as a tablet or a capsule comprising a fixed quantity of each one of the components) or can, on the other hand, be presented as separate formulations to be later combined for joint, sequential, or separate administration. The compositions or combinations of the invention also include the formulation as a kit-of-parts wherein the components are formulated separately but are packaged in the same container. Those skilled in the art will appreciate that the formulation of the different components in the case of the second pharmaceutical composition according to the invention may be similar, in other words, similarly formulated (in tablets or pills), which allows their administration by the same route. In the case where the different components of the invention are formulated separately, the two components can be presented in a blister. Each blister contains the drugs that must be consumed during the day. If the drugs must be administered several times a day, the drugs corresponding to each administration can be placed in different sections of the blister, preferably recording in each section of the blister the time of day when they should be administered. Alternatively, the components of the composition of the invention can be formulated differently so that the different components are differently administered. Thus, it is possible that the first component is formulated as a tablet or capsule for its oral administration and the second component is formulated for its intravenous administration or vice versa. The ratio between the components that are part of the compositions used in the second pharmaceutical composition according to the invention can be adjusted by the skilled person depending on the antitumor agent used in each particular case, as well as of the desired indication. Thus, the invention envisages compositions wherein the ratio between the quantities of the two components can range from 50:1 to 1:50, in particular from 20:1 to 1:20, from 1:10 to 10:1, or from 5:1 to 1:5.

The pharmaceutical compositions or combinations of the invention can be administered by any type of suitable route, such as by oral route, topical route, by inhalation or parenteral route so that the pharmaceutically acceptable excipients necessary for the formulation of the desired dosage form will be included. The preferred route of administration of said pharmaceutical compositions is the endovenous route.

"Oral route" is understood as the pharmaceutical composition incorporated into the organism after deglutition. In a particular embodiment, the pharmaceutical composition of the invention can be in a dosage form suitable for its administration by oral route, whether it is solid or liquid. The dosage forms suitable for their administration by oral route can be tablets, capsules, syrups or solutions, and can contain any conventional excipient known in the art, such as binders, for example syrup, acacia, gelatin, sorbitol or polyvinylpyrrolidone; filling agents, for example lactose, sugar, corn starch, calcium phosphate, sorbitol or glycine; lubricants for compression, for example, magnesium stearate; disintegrating agents, for example starch, polyvinylpyrrolidone, sodium glycolate of starch or microcrystalline cellulose; or pharmaceutically acceptable wetting agents such as sodium lauryl sulfate. The solid oral compositions can be prepared by means of conventional processes of mixing, filling or compressing. Repetitive mixing operations can be used to completely distribute the active agent in those compositions that use high amounts of filling agents. Said operations are conventional in the art. The tablets can be prepared, for example, by means of wet or dry granulation, and optionally coating them according to the processes known in the common pharmaceutical practice, particularly with an enteric coating.

On the other hand, "topical route" is understood as an administration by non-systemic route, and includes the application of a pharmaceutical composition of the invention externally on the epidermis, in the oral cavity and the instillation of said composition into ears, eyes and nose, and in which it does not significantly enter the blood stream. "Systemic route" is understood as the administration by oral route, intravenous route, intraperitoneal route and intramuscular route. "Inhalation" is understood as the administration by intranasal route and by oral inhalation. The dosage forms suitable for said administration, such as a formulation in aerosol or a meter dosed inhaler can be prepared by means of conventional techniques. In an embodiment the route of administration is the intranasal route.

As it is used herein, the term "parenteral", includes administration by intravenous route, intraperitoneal route, intramuscular route or subcutaneous route. Subcutaneous, intramuscular and intravenous dosage forms of parenteral administration are generally preferred.

In one embodiment, pharmaceutical compositions of the invention can be adapted for their parenteral administration, such as sterile solutions, suspensions or lyophilized products in the appropriate dosage unit form. The pharmaceutical compositions suitable for its injectable use include sterile aqueous solutions (when they are soluble in water), or dispersions and sterile powders for the extemporaneous preparation of sterile injectable solutions or dispersions. For its administration by intravenous route, some suitable carriers include saline solution buffered with phosphate (PBS). In all the cases, the composition must be sterile, and must be fluid to the point which that there exists easy ability for being injected. It must be stable in the preparation and storage conditions, and must be protected from the contamination action of microorganisms such as bacteria and fungi. The carrier can be a solvent or a dispersion medium which contains, for example, water, ethanol, a pharmaceutically acceptable polyol such as glycerol, propylene glycol, liquid polyethylene glycol and suitable mixtures thereof. Suitable fluidity can be maintained, for example, by means of using a coating such as lecithin, by means of maintaining the particle size required in the case of dispersion and by means of using surfactants. The prevention of the action of the microorganisms can be achieved by means of various antibacterial and antifungal agents, for example, parabens, chlorobutanol, phenol, ascorbic acid, thiomersal, and the like. In most cases, it will be preferable to include isotonic agents, for example, sugars; polyalcohols such as mannitol, sorbitol; or sodium chloride in the composition. The prolonged absorption of the injectable compositions may be caused by the inclusion of an agent which delays the absorption, for example, aluminum and gelatin monostearate.

The injectable sterile solutions can be prepared by incorporating the active compound in the required amount in a suitable solvent with one or a combination of the aforementioned ingredients, as needed, followed by sterilization by filtration through sterile membranes. Generally, the dispersions are prepared by incorporating the active compound in a sterile vehicle containing a basic dispersion medium and the rest of the ingredients required from among those previously listed. In the case of sterile powders for the preparation of injectable sterile solutions, the preferred preparation processes are vacuum drying and lyophilization which give rise to a powder with the active ingredient plus any desired additional ingredient from a previously filtered sterile solution thereof.

The pharmaceutical compositions of the invention can be suitably administered by means of pulse infusion, for example, with decreasing doses of the composition. Preferably, the dose is administered by means of injections, more preferably intravenous or subcutaneous injections, partly depending if the administration is acute or chronic.

In one embodiment, the first or second pharmaceutical compositions of the invention are prepared with carriers which will protect said polypeptide from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

The sustained release compositions also include preparations of antibody crystals suspended in suitable formulations which can maintain the crystals in suspension. These preparations, when they are injected by subcutaneous or intraperitoneal route may produce a sustained release effect. Other compositions also include antibodies trapped in liposomes. The liposomes containing such antibodies are prepared by means of known methods such as Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949.

Despite the fact that the polypeptide of the invention and the conjugates and fusion proteins containing the polypeptide of the invention are capable of translocating across biological membranes, the skilled person will understand that it may also be convenient to formulate the conjugates or fusion proteins comprising the polypeptides of the invention in nanoparticles.

As used herein, the term "nanoparticle" refers to any material having dimensions in the 1-1,000 nm range. In some embodiments, nanoparticles have dimensions in the 2-200 nm range, preferably in the 2-150 nm range, and even more preferably in the 2-100 nm range.

The nanoparticles may contribute to preserve the integrity of the polypeptide in the biological fluids until it reaches the target organ. Moreover, in the case of compositions comprising an antitumor agent, encapsulation of the composition may decrease secondary effects caused by the antitumor agent. Lastly, nanoparticles can also be modified so as to include moieties which allow the targeting of the nanoparticle to an organ of interest.

Thus, in another embodiment, the pharmaceutical compositions of the invention comprise the conjugates, fusion proteins and compositions according to the invention forming part of a nanoparticle.

Suitable nanoparticles that can be used in the context of the present invention include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube.

Targeted delivery can be achieved by the addition of ligands without compromising the ability of nanoparticles to deliver their polypeptide payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-β, nerve growth factor, albumin, HIV Tat peptide, RGD peptide, and insulin, as well as others.

It will be understood that the formulation of the product of the invention in a nanoparticle is not intended or is not solely intended for facilitating the access of the product to the interior of the cell but to protect the product from degradation and/or for facilitating targeting of the nanoparticle to the organ of interest.

The pharmaceutical compositions of the invention are suitable for the administration into any type of mammal, preferably a human being.

All the terms and embodiments previously described are equally applicable to this aspect of the invention.

Medical Uses

In another aspect, the invention relates to a polypeptide or functional equivalent variant of said polypeptide according to the invention, a conjugate according to the invention, a polynucleotide according to the invention, a vector according to the invention, a host cell according to the invention or a pharmaceutical composition according to the invention for use in medicine.

In another aspect, the invention relates to a polypeptide or functional equivalent variant of said polypeptide according to the invention, a conjugate according to the invention, a polynucleotide according to the invention, a vector according to the invention, a host cell according to the invention or a pharmaceutical composition according to the invention for use in the prevention and/or treatment of cancer.

Alternatively, the invention relates to a method for preventing and/or treating cancer comprising administering to a subject in need thereof a therapeutically effective amount of a polypeptide or functional equivalent variant of said polypeptide according to the invention, a conjugate according to the invention, a polynucleotide according to the invention, a vector according to the invention, a host cell according to the invention or a pharmaceutical composition according to the invention.

Alternatively, the invention relates to the use of a polypeptide or functional equivalent variant of said polypeptide according to the invention, a conjugate according to the invention, a polynucleotide according to the invention, a vector according to the invention, a host cell according to the invention or a pharmaceutical composition according to the invention for the preparation of a medicament for the prevention and/or treatment of cancer.

"Prevention" is understood as the administration of a compound in an initial or early stage of the disease, or to also prevent its onset.

The term "treatment" is used to designate the administration of a compound to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

A "subject," as used herein, includes any animal that has a cancer or exhibits a symptom of cancer, or is at risk for having a cancer or exhibiting a symptom of cancer. Suitable subjects (patients) include laboratory animals (such as mouse, rat, rabbit, or guinea pig), farm animals, and domestic animals or pets (such as a cat or dog). Non-human primates and, preferably, human patients, are included.

The term "cancer" is referred to a disease characterized by uncontrolled cell division (or by an increase of survival or apoptosis resistance), by the ability of said cells to invade other neighbouring tissues (invasion) or by the spread to other areas of the body where the cells are not normally located (metastasis) through the lymphatic and blood vessels. Depending on whether or not tumours can spread by invasion and metastasis, they are classified as being either benign or malignant: benign tumours are tumours that cannot spread by invasion or metastasis, i.e., they only grow locally; whereas malignant tumours are tumours that are capable of spreading by invasion and metastasis. The methods according to the present invention are useful for the treatment of local and malignant tumours. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyo sarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art. In a preferred embodiment, the cancer treated is lung cancer, preferably lung adenocarcinoma, more preferably a KRas-driven lung adenocarcinoma.

In a preferred embodiment the cancer is a solid tumor.

All combinations of compounds of the invention and types of cancer are included in the present invention.

In a preferred embodiment, the cancer is selected from the group consisting of glioblastoma and Non-Small-Cell-Lung-Cancer.

"Glioblastoma", also known as glioblastoma and grade IV astrocytoma, is the most common and most aggressive cancer that begins within the brain.

The term "NSCLC" or "non-small cell lung cancer", as used herein, refers to a group of heterogeneous diseases grouped together because their prognosis and management is roughly identical according to the histological classification of the World Health Organization/International Association for the Study of Lung Cancer (Travis W D et al. Histological typing of lung and pleural tumours. 3$^{rd}$ ed. Berlin: Springer-Verlag, 1999):

1. squamous cell carcinoma (SCC), accounting for 30% to 40% of NSCLC, starts in the larger breathing tubes but grows slower meaning that the size of these tumours varies on diagnosis.
2. adenocarcinoma is the most common subtype of NSCLC, accounting for 50% to 60% of NSCLC, which starts near the gas-exchanging surface of the lung and which includes a subtype, the bronchioalveolar carcinoma, which may have different responses to treatment.
3. large cell carcinoma is a fast-growing form that grows near the surface of the lung. It is primarily a diagnosis of exclusion, and when more investigation is done, it is usually reclassified to squamous cell carcinoma or adenocarcinoma.
4. adenosquamous carcinoma is a type of cancer that contains two types of cells: squamous cells (thin, flat cells that line certain organs) and gland-like cells.
5. carcinomas with pleomorphic, sarcomatoid or sarcomatous elements. This is a group of rare tumours reflecting a continuum in histological heterogeneity as well as epithelial and mesenchymal differentiation.
6. carcinoid tumour is a slow-growing neuroendocrine lung tumour and begins in cells that are capable of releasing a hormone in response to a stimulus provided by the nervous system.
7. carcinomas of salivary gland type begin in salivary gland cells located inside the large airways of the lung.
8. unclassified carcinomas include cancers that do not fit into any of the aforementioned lung cancer categories.

The invention also relates to:

[1]. A polypeptide comprising the polypeptide of SEQ ID NO: 1 wherein the residue X at position 89 of SEQ ID NO: 1 is not a cysteine, or a functionally equivalent variant of said polypeptide.

[2]. The polypeptide according to [1], wherein said polypeptide consists of the polypeptide of SEQ ID NO: 1 wherein the residue X at position 89 of SEQ ID NO: 1 is not a cysteine or consists of a functionally equivalent variant of said polypeptide.

[3]. The polypeptide according to [1] or [2], wherein the residue X at position 89 of SEQ ID NO: 1 is serine.

[4]. The polypeptide according to [3] consisting of SEQ ID NO: 4.

[5]. A conjugate comprising:
   a. the polypeptide or functionally equivalent variant of said polypeptide according to any one of [1]-[4] and
   b. a chemical moiety that facilitates cellular uptake of the polypeptide or of the functionally equivalent variant of said polypeptide.

[6]. The conjugate according to [5], wherein the chemical moiety that facilitates cellular uptake of the polypeptide or of the functionally equivalent variant of said polypeptide is a cell penetrating peptide sequence and wherein said cell penetrating peptide sequence and said polypeptide or the functionally equivalent variant of said polypeptide form a fusion protein.

[7]. The conjugate according to [6], wherein the cell-penetrating peptide sequence is selected from the group consisting of GRKKRRQRRR (SEQ ID NO: 38) and RRRRRRLR (SEQ ID NO: 39).

[8]. The conjugate according to any one of [5] to [7] further comprising a further nuclear-localization signal, particularly the nuclear localization signal is selected from the group consisting of PKKKRKV (SEQ ID NO: 6), PAAKRVKLD (SEQ ID NO: 54) and KRPAATKKAGQAKKKK (SEQ ID NO: 7).

[9]. A polynucleotide encoding a polypeptide according to any of [1] to [4] or a conjugate according to any one of [5] to [8].

[10]. A vector comprising a polynucleotide according to [9].

[11]. A host cell comprising a polypeptide according to any one of [1] to [4], a conjugate according to any one of [5] to [8], a polynucleotide according to [9] or a vector according to [10].

[12]. A pharmaceutical composition comprising a pharmaceutically effective amount of a polypeptide or functional equivalent variant of said polypeptide according to any one of [1] to [4], a conjugate according to any one of [5] to [8], a polynucleotide according to [9], a vector according to [10] or a host cell according to [11], and a pharmaceutically acceptable excipient.

[13]. A polypeptide or functional equivalent variant of said polypeptide according to any one of [1] to [4], a conjugate according to any one of [5] to [8], a polynucleotide according to [9], a vector according to [10], a host cell according to [11] or a pharmaceutical composition according to [12] for use in medicine.

[14]. A polypeptide or functional equivalent variant thereof according to any one of [1] to [4], a conjugate according to any one of [5] to [8], a polynucleotide according to [9], a vector according to [10], a host cell according to [11] or a pharmaceutical composition according to [12] for use in the prevention and/or treatment of cancer.

[15]. The polypeptide or functional equivalent variant thereof, the conjugate, the polynucleotide, the vector, the host cell or the pharmaceutical composition for use according to [14], wherein the cancer is selected from the group consisting of glioblastoma and Non-Small-Cell-Lung-Cancer.

All the terms and embodiments previously described are equally applicable to this aspect of the invention.

The invention is detailed below by means of the following examples which are merely illustrative and by no means limiting for the scope of the invention.

EXAMPLES

Materials and Methods

Transfection of Cells with Omomyc and OmoCS mRNA mRNA for Omomyc and OmoCS mutant was purchased from Trilink Biotechnologies at concentrations of 0.782 mg/mL and 0.876 mg/mL respectively (ARCA capped and fully substituted with 5-methyl-C and pseudo-U modified). Either the Omomyc or the OmoCS DNA sequence was introduced into a vector downstream the T7 RNA polymerase promoter and a poly(T) tail located at the 3p end. 5-Methylcytidine-5'-triphosphate and Pseudouridine-5'-triphosphate modified-RNA was produced through in vitro transcription using a T7 RNA polymerase. RNA was also capped using [3 '-0-Me-m7G(5')ppp(5')G] RNA cap structure analog. Template DNA vector was degraded using DNAse and residual triphosphate removed by a phosphatase treatment. The RNA product was then purified and the integrity and quantity assessed by agarose-gel electrophoresis and Nanodrop respectively. RNA was stored at −80° C. Lipofectamine MessengerMAX Transfection Reagent was purchased from Thermo Fisher Scientific. A549 and U87 cell lines were seeded at 500 and 1000 cell per well, respectively, in 96 well-plates. Cells were grown in Dulbecco's Modified Eagle Medium (DMEM) supplemented with 10% fetal bovine serum (FBS) and 1% L-glutamine (complete media). After 24 hours, cells were transfected with lipofectamine-mRNA complexes. 3 µg of mRNA for each 2 µL of lipofectamine were separately diluted in serum-free media and incubated for 10 minutes. mRNA and lipofectamine dilutions were then mixed and incubated for 5 minutes to allow complexes to form.

Wells were washed with serum-free medium twice. Cells were serially diluted starting from 1 µg to 0.0625 µg of mRNA per well in 100 µL of total serum-free media. For each concentration, control cells were treated with lipofectamine only and triplicates were used for each condition. After 4 hours of transfection, serum-free media and mRNA-lipofectamine complexes were removed from the wells and substituted with complete media. Cells were incubated for 3 days. Then, viability was assessed using CellTiter-Blue from Promega. Absorbance relative to non-treated wells was calculated for each condition. Statistical significance was calculated by t-test.

Transfection of cells with OmoCS and OmoCA mRNA mRNA for OmoCS and OmoCA mutants was purchased from Trilink Biotechnologies (ARCA capped and fully substituted with 5-methyl-C and pseudo-U modified). mRNA concentrations for OmoCS and OmoCA were determined at 0.845 mg/mL and 0.832 mg/mL respectively using a Nanodrop. Lipofectamine MessengerMAX Transfection Reagent was purchased from Thermo Fisher Scientific. A549 cell were seeded at 500 cell per well in 96 well-plate. Cells were grown in Roswell Park Memorial Institute (RPMI) medium supplemented with 10% of fetal bovine serum (FBS) and 1% of L-glutamine (complete media). After 24 hours, cells were transfected with lipofectamine-mRNA complexes. 2 µg of mRNA for each 1.54 of lipofectamine were separately diluted in serum-free media and incubated for 10 minutes. mRNA and lipofectamine dilutions were then mixed and incubated for 5 minutes to allow complexes to form. Wells were washed with serum-free medium twice. Cells were treated with serial 1:2 dilutions starting at 1 µg of mRNA per well in 504 of total serum-free media (200 nM). For each concentration, cells were either untreated (Non-treated) or treated with lipofectamine only (Lipo only) as control wells. Triplicates were performed for each condition. After 4 hours of transfection, serum-free media and mRNA-lipofectamine complexes were removed from the wells and substituted with complete RPMI media. Cells were incubated for 3 days. At that point, cell density was assessed using crystal violet staining. Absorbance relative to non-treated wells was calculated for each concentration.

Example 1

Surprisingly, OmoCS mutant displays higher inhibition of cell growth compared to the original Omomyc sequence at low concentration (FIG. 1). This improved efficacy compared to the original Omomyc sequence could be at least partially explained by the hypothesis that oxydized interfacial cysteine of the Omomyc homodimer would prevent heterodimerization of Omomyc with Myc or with Max, limiting Omomyc's activity to mere competition for E-box binding. Instead, the OmoCS mutant would favour other biological activities of Omomyc by promoting the formation of heterodimeric populations.

Example 2

Figure 2:
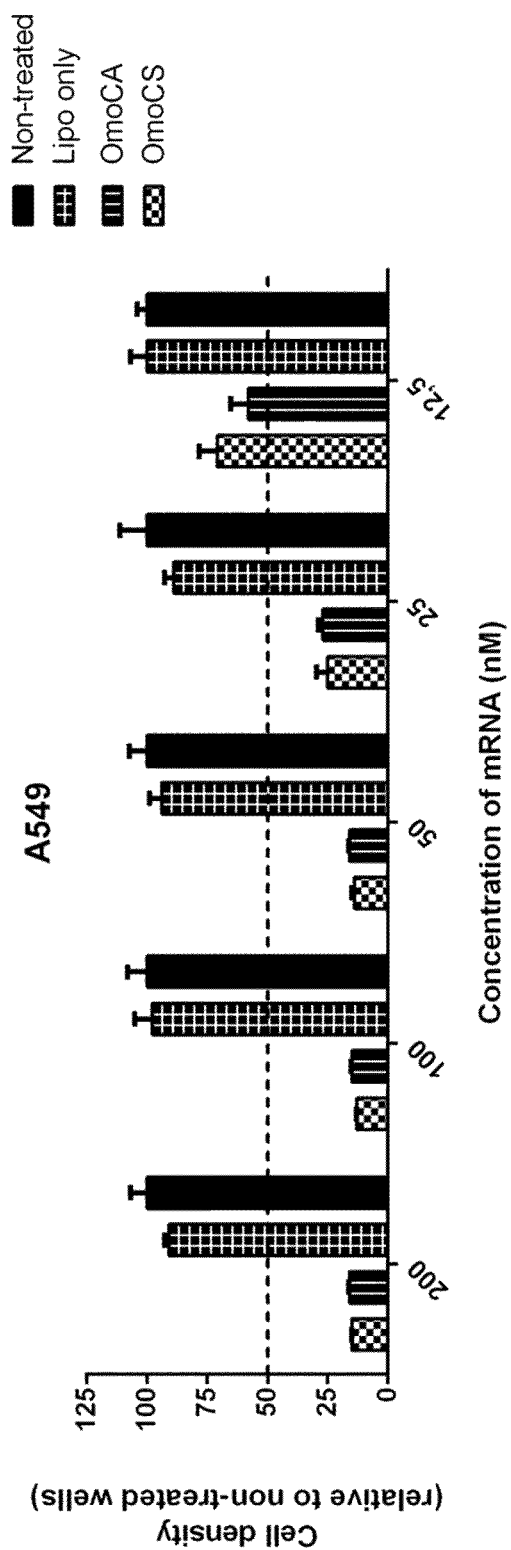
FIG. 2. Cell density assay shows that OmoCA (harbouring the C98A change) inhibits the growth of A549 lung adenocarcinoma cells as efficiently as OmoCS (harbouring the C98S change) at lower concentration. Lipofectamine (Lipo) causes no effect.

Surprisingly, OmoCA mutant behaves exactly as OmoCS in the same proliferation assay (FIG. 2).

The invention claimed is:

1. A polypeptide comprising the polypeptide of SEQ ID NO: 1, or a functionally equivalent variant thereof, wherein the residue X at position 89 of SEQ ID NO: 1 is not a cysteine, and wherein the functionally equivalent variant of SEQ ID NO: 1 has a threonine at the position corresponding to position 61 of SEQ ID NO: 1, an isoleucine at the position corresponding to position 68 of SEQ ID NO: 1, a glutamine at the position corresponding to position 74 of SEQ ID NO: 1, and an asparagine at the position corresponding to position 75 of SEQ ID NO: 1.

2. The polypeptide according to claim 1, wherein the functionally equivalent variant is any polypeptide which results from the deletion, insertion, or addition of one or more amino acids with respect to the polypeptide of SEQ ID NO: 1, or which results from a chemical modification of the polypeptide of SEQ ID NO: 1 and which substantially preserves the tumor suppressor activity of the polypeptide of SEQ ID NO: 1.

3. The polypeptide according to claim 1, wherein said polypeptide consists of the polypeptide of SEQ ID NO: 1.

4. The polypeptide according to claim 1, wherein said polypeptide consists of the polypeptide of SEQ ID NO: 3 wherein the residue X at position 90 of SEQ ID NO: 3 is not a cysteine.

5. The polypeptide according to claim 1, wherein the residue X at position 89 of SEQ ID NO: 1 is serine or alanine.

6. The polypeptide according to claim 5, wherein said polypeptide consists of the polypeptide of SEQ ID NO: 4.

7. A conjugate comprising:
   a. the polypeptide, or a functionally equivalent variant thereof, according to claim 1 and
   b. a chemical moiety that facilitates cellular uptake of the polypeptide, or the functionally equivalent variant thereof.

8. The conjugate according to claim 7, wherein the chemical moiety that facilitates cellular uptake of the polypeptide, or the functionally equivalent variant thereof, is a cell penetrating peptide sequence, wherein said cell penetrating peptide sequence and said polypeptide, or the functionally equivalent variant thereof, form a fusion protein.

9. The conjugate according to claim 8, wherein the cell penetrating peptide sequence is selected from the group consisting of GRKKRRQRRR (SEQ ID NO: 38) and RRRRRRLR (SEQ ID NO: 39).

10. The conjugate according to claim 7, further comprising a nuclear-localization signal.

11. The conjugate according to claim 10, wherein the nuclear localization signal is selected from the group consisting of PKKKRKV (SEQ ID NO: 6), PAAKRVKLD (SEQ ID NO: 54), and KRPAATKKAGQAKKKK (SEQ ID NO: 7).

12. A polynucleotide encoding a polypeptide according to claim 1.

13. A vector comprising a polynucleotide according to claim 12.

14. A vector comprising a polynucleotide encoding a conjugate according to claim 7.

15. A host cell comprising a polypeptide according to claim 1.

16. A host cell comprising a conjugate according to claim 7.

17. A pharmaceutical composition comprising a polypeptide, or a functionally equivalent variant thereof, according to claim 1, and a pharmaceutically acceptable excipient.

18. A pharmaceutical composition comprising a conjugate according to claim 7, and a pharmaceutically acceptable excipient.

19. A method for treating cancer, comprises administering to a subject in need thereof a therapeutically effective amount of a polypeptide, or a functionally equivalent variant thereof, according to claim 1.

20. A method for treating cancer, comprises administering to a subject in need thereof a therapeutically effective amount of a conjugate according to claim 7.

* * * * *

SEQUENCE LISTING

<160> NUMBER OF SEQ ID NOS: 64

<210> SEQ ID NO 1
<211> LENGTH: 90
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (89)..(89)
<223> OTHER INFORMATION: Xaa may be any amino acid except Cysteine

<400> SEQUENCE: 1

Thr Glu Glu Asn Val Lys Arg Arg Thr His Asn Val Leu Glu Arg Gln
1               5                   10                  15

Arg Arg Asn Glu Leu Lys Arg Ser Phe Phe Ala Leu Arg Asp Gln Ile
            20                  25                  30

Pro Glu Leu Glu Asn Asn Glu Lys Ala Pro Lys Val Val Ile Leu Lys
        35                  40                  45

Lys Ala Thr Ala Tyr Ile Leu Ser Val Gln Ala Glu Thr Gln Lys Leu
    50                  55                  60

Ile Ser Glu Ile Asp Leu Leu Arg Lys Gln Asn Glu Gln Leu Lys His
65                  70                  75                  80

Lys Leu Glu Gln Leu Arg Asn Ser Xaa Ala
                85                  90

<210> SEQ ID NO 2
<211> LENGTH: 90
<212> TYPE: PRT
<213> ORGANISM: Artificial Sequence
<220> FEATURE:
<223> OTHER INFORMATION: Polypeptide

<400> SEQUENCE: 2

Thr Glu Glu Asn Val Lys Arg Arg Thr His Asn Val Leu Glu Arg Gln
1               5                   10                  15

Arg Arg Asn Glu Leu Lys Arg Ser Phe Phe Ala Leu Arg Asp Gln Ile
            20                  25                  30

Pro Glu Leu Glu Asn Asn Glu Lys Ala Pro Lys Val Val Ile Leu Lys
        35                  40                  45

Lys Ala Thr Ala Tyr Ile Leu Ser Val Gln Ala Glu Thr Gln Lys Leu
    50                  55                  60

Ile Ser Glu Ile Asp Leu Leu Arg Lys Gln Asn Glu Gln Leu Lys His
65                  70                  75                  80

Lys Leu Glu Gln Leu Arg Asn Ser Ser Ala
                85                  90

<210> SEQ ID NO 3
<211> LENGTH: 91
<212> TYPE: PRT
<213> ORGANISM: Artificial Sequence
<220> FEATURE:
<223> OTHER INFORMATION: Polypeptide
<220> FEATURE:
<221> NAME/KEY: VARIANT
<222> LOCATION: (90)..(90)
<223> OTHER INFORMATION: X may be any amino acid except Cysteine

```
<400> SEQUENCE: 3

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
50                  55                  60

Leu Ile Ser Glu Ile Asp Leu Leu Arg Lys Gln Asn Glu Gln Leu Lys
65                  70                  75                  80

His Lys Leu Glu Gln Leu Arg Asn Ser Xaa Ala
                85                  90

<210> SEQ ID NO 4
<211> LENGTH: 91
<212> TYPE: PRT
<213> ORGANISM: Artificial Sequence
<220> FEATURE:
<223> OTHER INFORMATION: Polypeptide

<400> SEQUENCE: 4

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
50                  55                  60

Leu Ile Ser Glu Ile Asp Leu Leu Arg Lys Gln Asn Glu Gln Leu Lys
65                  70                  75                  80

His Lys Leu Glu Gln Leu Arg Asn Ser Ser Ala
                85                  90

<210> SEQ ID NO 5
<211> LENGTH: 454
<212> TYPE: PRT
<213> ORGANISM: Homo sapiens

<400> SEQUENCE: 5

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125
```

```
Ser Phe Ile Cys Asp Pro Asp Asp Glu Thr Phe Ile Lys Asn Ile Ile
    130                 135                 140
Ile Gln Asp Cys Met Trp Ser Gly Phe Ser Ala Ala Lys Leu Val
145                 150                 155                 160
Ser Glu Lys Leu Ala Ser Tyr Gln Ala Ala Arg Lys Asp Ser Gly Ser
                165                 170                 175
Pro Asn Pro Ala Arg Gly His Ser Val Cys Ser Thr Ser Ser Leu Tyr
                180                 185                 190
Leu Gln Asp Leu Ser Ala Ala Ser Glu Cys Ile Asp Pro Ser Val
    195                 200                 205
Val Phe Pro Tyr Pro Leu Asn Asp Ser Ser Pro Lys Ser Cys Ala
    210                 215                 220
Ser Gln Asp Ser Ser Ala Phe Ser Pro Ser Ser Asp Ser Leu Leu Ser
225                 230                 235                 240
Ser Thr Glu Ser Ser Pro Gln Gly Ser Pro Glu Pro Leu Val Leu His
                245                 250                 255
Glu Glu Thr Pro Pro Thr Thr Ser Ser Asp Ser Glu Glu Glu Gln Glu
                260                 265                 270
Asp Glu Glu Glu Ile Asp Val Val Ser Val Glu Lys Arg Gln Ala Pro
            275                 280                 285
Gly Lys Arg Ser Glu Ser Gly Ser Pro Ser Ala Gly Gly His Ser Lys
            290                 295                 300
Pro Pro His Ser Pro Leu Val Leu Lys Arg Cys His Val Ser Thr His
305                 310                 315                 320
Gln His Asn Tyr Ala Ala Pro Pro Ser Thr Arg Lys Asp Tyr Pro Ala
                325                 330                 335
Ala Lys Arg Val Lys Leu Asp Ser Val Arg Val Leu Arg Gln Ile Ser
                340                 345                 350
Asn Asn Arg Lys Cys Thr Ser Pro Arg Ser Ser Asp Thr Glu Glu Asn
            355                 360                 365
Val Lys Arg Arg Thr His Asn Val Leu Glu Arg Gln Arg Arg Asn Glu
        370                 375                 380
Leu Lys Arg Ser Phe Phe Ala Leu Arg Asp Gln Ile Pro Glu Leu Glu
385                 390                 395                 400
Asn Asn Glu Lys Ala Pro Lys Val Val Ile Leu Lys Lys Ala Thr Ala
                405                 410                 415
Tyr Ile Leu Ser Val Gln Ala Glu Glu Gln Lys Leu Ile Ser Glu Glu
                420                 425                 430
Asp Leu Leu Arg Lys Arg Arg Glu Gln Leu Lys His Lys Leu Glu Gln
            435                 440                 445
Leu Arg Asn Ser Cys Ala
    450

<210> SEQ ID NO 6
<211> LENGTH: 7
<212> TYPE: PRT
<213> ORGANISM: Artificial Sequence
<220> FEATURE:
<223> OTHER INFORMATION: SV40 large T Antigen NLS

<400> SEQUENCE: 6

Pro Lys Lys Lys Arg Lys Val
1               5
```

```
<210> SEQ ID NO 7
<211> LENGTH: 16
<212> TYPE: PRT
<213> ORGANISM: Artificial Sequence
<220> FEATURE:
<223> OTHER INFORMATION: Nucleoplasmin NLS

<400> SEQUENCE: 7

Lys Arg Pro Ala Ala Thr Lys Lys Ala Gly Gln Ala Lys Lys Lys Lys
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: CBP80 NLS

<400> SEQUENCE: 8

Arg Arg Arg His Ser Asp Glu Asn Asp Gly Gly Gln Pro His Lys Arg
1               5                   10                  15

Arg Lys

<210> SEQ ID NO 9
<211> LENGTH: 11
<212> TYPE: PRT
<213> ORGANISM: Artificial Sequence
<220> FEATURE:
<223> OTHER INFORMATION: HIV-I Rev protein NLS

<400> SEQUENCE: 9

Arg Gln Ala Arg Arg Asn Arg Arg Arg Trp Glu
1               5                   10

<210> SEQ ID NO 10
<211> LENGTH: 18
<212> TYPE: PRT
<213> ORGANISM: Artificial Sequence
<220> FEATURE:
<223> OTHER INFORMATION: HTLV-I Rex

<400> SEQUENCE: 10

Met Pro Lys Thr Arg Arg Arg Pro Arg Arg Ser Gln Arg Lys Arg Pro
1               5                   10                  15

Pro Thr

<210> SEQ ID NO 11
<211> LENGTH: 37
<212> TYPE: PRT
<213> ORGANISM: Artificial Sequence
<220> FEATURE:
<223> OTHER INFORMATION: hnRNP A NLS

<400> SEQUENCE: 11

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Lys Pro Arg
            20                  25                  30

Asn Gln Gly Gly Tyr
        35

<210> SEQ ID NO 12
<211> LENGTH: 43
<212> TYPE: PRT
<213> ORGANISM: Artificial Sequence
```

```
<220> FEATURE:
<223> OTHER INFORMATION: rpL23a NLS

<400> SEQUENCE: 12

Val His Ser His Lys Lys Lys Ile Arg Thr Ser Pro Thr Phe Thr
1               5                   10                  15

Thr Pro Lys Thr Leu Arg Leu Arg Arg Gln Pro Lys Tyr Pro Arg Lys
            20                  25                  30

Ser Ala Pro Arg Arg Asn Lys Leu Asp His Tyr
            35                  40

<210> SEQ ID NO 13
<211> LENGTH: 4
<212> TYPE: PRT
<213> ORGANISM: Artificial Sequence
<220> FEATURE:
<223> OTHER INFORMATION: NLS sequence
<220> FEATURE:
<221> NAME/KEY: VARIANT
<222> LOCATION: (2)..(2)
<223> OTHER INFORMATION: replace="R or K"
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: replace="R or K"

<400> SEQUENCE: 13

Leu Xaa Xaa Xaa
1

<210> SEQ ID NO 14
<211> LENGTH: 16
<212> TYPE: PRT
<213> ORGANISM: Artificial Sequence
<220> FEATURE:
<223> OTHER INFORMATION: CPP found in Drosophila antennapedia protein

<400> SEQUENCE: 14

Arg Gln Ile Lys Ile Trp Phe Gln Asn Arg Arg Met Lys Trp Lys Lys
1               5                   10                  15

<210> SEQ ID NO 15

<400> SEQUENCE: 15

000

<210> SEQ ID NO 16
<211> LENGTH: 24
<212> TYPE: PRT
<213> ORGANISM: Artificial Sequence
<220> FEATURE:
<223> OTHER INFORMATION: CPP of Bac-7

<400> SEQUENCE: 16

Arg Arg Ile Arg Pro Arg Pro Pro Arg Leu Pro Arg Pro Arg Pro Arg
1               5                   10                  15

Pro Leu Pro Phe Pro Arg Pro Gly
            20
```

```
<210> SEQ ID NO 17
<211> LENGTH: 9
<212> TYPE: PRT
<213> ORGANISM: Artificial Sequence
<220> FEATURE:
<223> OTHER INFORMATION: CPP of the HIV-1 TAT protein

<400> SEQUENCE: 17

Arg Lys Lys Arg Arg Gln Arg Arg Arg
1               5

<210> SEQ ID NO 18
<211> LENGTH: 13
<212> TYPE: PRT
<213> ORGANISM: Artificial Sequence
<220> FEATURE:
<223> OTHER INFORMATION: CPP of the HIV-1 TAT protein

<400> SEQUENCE: 18

Gly Arg Lys Lys Arg Arg Gln Arg Arg Arg Thr Pro Gln
1               5                   10

<210> SEQ ID NO 19
<211> LENGTH: 11
<212> TYPE: PRT
<213> ORGANISM: Artificial Sequence
<220> FEATURE:
<223> OTHER INFORMATION: CPP of the HIV-1 TAT protein

<400> SEQUENCE: 19

Tyr Gly Arg Lys Lys Arg Arg Gln Arg Arg Arg
1               5                   10

<210> SEQ ID NO 20
<211> LENGTH: 20
<212> TYPE: PRT
<213> ORGANISM: Artificial Sequence
<220> FEATURE:
<223> OTHER INFORMATION: CPP of S413-PV peptide

<400> SEQUENCE: 20

Ala Leu Trp Lys Thr Leu Leu Lys Lys Val Leu Lys Ala Pro Lys Lys
1               5                   10                  15

Lys Arg Lys Val
            20

<210> SEQ ID NO 21
<211> LENGTH: 15
<212> TYPE: PRT
<213> ORGANISM: Artificial Sequence
<220> FEATURE:
<223> OTHER INFORMATION: CPP of penetratin

<400> SEQUENCE: 21

Arg Gln Ile Lys Trp Phe Gln Asn Arg Arg Met Lys Trp Lys Lys
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: CPP of SynB1
```

```
<400> SEQUENCE: 22

Arg Gly Gly Arg Leu Ser Tyr Ser Arg Arg Phe Ser Thr Ser Thr
1               5                   10                  15

Gly Arg

<210> SEQ ID NO 23
<211> LENGTH: 10
<212> TYPE: PRT
<213> ORGANISM: Artificial Sequence
<220> FEATURE:
<223> OTHER INFORMATION: CPP of SynB3

<400> SEQUENCE: 23

Arg Arg Leu Ser Tyr Ser Arg Arg Arg Phe
1               5                   10

<210> SEQ ID NO 24
<211> LENGTH: 12
<212> TYPE: PRT
<213> ORGANISM: Artificial Sequence
<220> FEATURE:
<223> OTHER INFORMATION: CPP of PTD-4

<400> SEQUENCE: 24

Pro Ile Arg Arg Arg Lys Lys Leu Arg Arg Leu Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: CPP of PTD-5

<400> SEQUENCE: 25

Arg Arg Gln Arg Arg Thr Ser Lys Leu Met Lys Arg
1               5                   10

<210> SEQ ID NO 26
<211> LENGTH: 15
<212> TYPE: PRT
<213> ORGANISM: Artificial Sequence
<220> FEATURE:
<223> OTHER INFORMATION: CPP of the FHV Coat-(35-49)

<400> SEQUENCE: 26

Arg Arg Arg Arg Asn Arg Thr Arg Arg Asn Arg Arg Arg Val Arg
1               5                   10                  15

<210> SEQ ID NO 27
<211> LENGTH: 19
<212> TYPE: PRT
<213> ORGANISM: Artificial Sequence
<220> FEATURE:
<223> OTHER INFORMATION: CPP of BMV Gag-(7-25)

<400> SEQUENCE: 27

Lys Met Thr Arg Ala Gln Arg Arg Ala Ala Ala Arg Arg Asn Arg Trp
1               5                   10                  15

Thr Ala Arg

<210> SEQ ID NO 28
<211> LENGTH: 13
<212> TYPE: PRT
<213> ORGANISM: Artificial Sequence
```

```
<220> FEATURE:
<223> OTHER INFORMATION: CPP of HTLV-II Rex-(4-16)

<400> SEQUENCE: 28

Thr Arg Arg Gln Arg Thr Arg Arg Ala Arg Arg Asn Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: CPP of D-Tat

<400> SEQUENCE: 29

Gly Arg Lys Lys Arg Arg Gln Arg Arg Arg Pro Pro Gln
1               5                   10

<210> SEQ ID NO 30
<211> LENGTH: 13
<212> TYPE: PRT
<213> ORGANISM: Artificial Sequence
<220> FEATURE:
<223> OTHER INFORMATION: CPP R9-Tat

<400> SEQUENCE: 30

Gly Arg Arg Arg Arg Arg Arg Arg Arg Arg Pro Pro Gln
1               5                   10

<210> SEQ ID NO 31
<211> LENGTH: 17
<212> TYPE: PRT
<213> ORGANISM: Artificial Sequence
<220> FEATURE:
<223> OTHER INFORMATION: CPP of MAP

<400> SEQUENCE: 31

Lys Leu Ala Leu Lys Leu Ala Leu Lys Leu Ala Leu Ala Leu Lys Leu
1               5                   10                  15

Ala

<210> SEQ ID NO 32
<211> LENGTH: 27
<212> TYPE: PRT
<213> ORGANISM: Artificial Sequence
<220> FEATURE:
<223> OTHER INFORMATION: CPP of SBP

<400> SEQUENCE: 32

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 33
<211> LENGTH: 27
<212> TYPE: PRT
<213> ORGANISM: Artificial Sequence
<220> FEATURE:
<223> OTHER INFORMATION: CPP of FBP
```

```
<400> SEQUENCE: 33

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 34
<211> LENGTH: 27
<212> TYPE: PRT
<213> ORGANISM: Artificial Sequence
<220> FEATURE:
<223> OTHER INFORMATION: CPP of MPG

<400> SEQUENCE: 34

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 35
<211> LENGTH: 27
<212> TYPE: PRT
<213> ORGANISM: Artificial Sequence
<220> FEATURE:
<223> OTHER INFORMATION: CPP of MPG(ENLS)

<400> SEQUENCE: 35

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 36
<211> LENGTH: 21
<212> TYPE: PRT
<213> ORGANISM: Artificial Sequence
<220> FEATURE:
<223> OTHER INFORMATION: CPP of Pep-1

<400> SEQUENCE: 36

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 37
<211> LENGTH: 21
<212> TYPE: PRT
<213> ORGANISM: Artificial Sequence
<220> FEATURE:
<223> OTHER INFORMATION: CPP of Pep-2

<400> SEQUENCE: 37

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 38
<211> LENGTH: 10
<212> TYPE: PRT
<213> ORGANISM: Artificial Sequence
<220> FEATURE:
<223> OTHER INFORMATION: CPP
```

```
<400> SEQUENCE: 38

Gly Arg Lys Lys Arg Arg Gln Arg Arg Arg
1               5                   10

<210> SEQ ID NO 39
<211> LENGTH: 8
<212> TYPE: PRT
<213> ORGANISM: Artificial Sequence
<220> FEATURE:
<223> OTHER INFORMATION: CPP

<400> SEQUENCE: 39

Arg Arg Arg Arg Arg Arg Leu Arg
1               5

<210> SEQ ID NO 40
<211> LENGTH: 12
<212> TYPE: PRT
<213> ORGANISM: Artificial Sequence
<220> FEATURE:
<223> OTHER INFORMATION: CPP

<400> SEQUENCE: 40

Arg Arg Gln Arg Arg Thr Ser Lys Leu Met Lys Arg
1               5                   10

<210> SEQ ID NO 41
<211> LENGTH: 27
<212> TYPE: PRT
<213> ORGANISM: Artificial Sequence
<220> FEATURE:
<223> OTHER INFORMATION: CPP

<400> SEQUENCE: 41

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 42
<211> LENGTH: 33
<212> TYPE: PRT
<213> ORGANISM: Artificial Sequence
<220> FEATURE:
<223> OTHER INFORMATION: CPP

<400> SEQUENCE: 42

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 43
<211> LENGTH: 16
<212> TYPE: PRT
<213> ORGANISM: Artificial Sequence
<220> FEATURE:
<223> OTHER INFORMATION: CPP

<400> SEQUENCE: 43

Arg Gln Ile Lys Ile Trp Phe Gln Asn Arg Arg Met Lys Trp Lys Lys
1               5                   10                  15
```

```
<210> SEQ ID NO 44
<211> LENGTH: 11
<212> TYPE: PRT
<213> ORGANISM: Artificial Sequence
<220> FEATURE:
<223> OTHER INFORMATION: CPP

<400> SEQUENCE: 44

Tyr Gly Arg Lys Lys Arg Arg Gln Arg Arg Arg
1               5                   10

<210> SEQ ID NO 45
<211> LENGTH: 8
<212> TYPE: PRT
<213> ORGANISM: Artificial Sequence
<220> FEATURE:
<223> OTHER INFORMATION: CPP

<400> SEQUENCE: 45

Arg Lys Lys Arg Arg Gln Arg Arg
1               5

<210> SEQ ID NO 46
<211> LENGTH: 11
<212> TYPE: PRT
<213> ORGANISM: Artificial Sequence
<220> FEATURE:
<223> OTHER INFORMATION: CPP

<400> SEQUENCE: 46

Tyr Ala Arg Ala Ala Ala Arg Gln Ala Arg Ala
1               5                   10

<210> SEQ ID NO 47
<211> LENGTH: 11
<212> TYPE: PRT
<213> ORGANISM: Artificial Sequence
<220> FEATURE:
<223> OTHER INFORMATION: CPP

<400> SEQUENCE: 47

Thr His Arg Leu Pro Arg Arg Arg Arg Arg Arg
1               5                   10

<210> SEQ ID NO 48
<211> LENGTH: 11
<212> TYPE: PRT
<213> ORGANISM: Artificial Sequence
<220> FEATURE:
<223> OTHER INFORMATION: CPP

<400> SEQUENCE: 48

Gly Gly Arg Arg Ala Arg Arg Arg Arg Arg Arg
1               5                   10

<210> SEQ ID NO 49
<211> LENGTH: 9
<212> TYPE: PRT
<213> ORGANISM: Artificial Sequence
<220> FEATURE:
<223> OTHER INFORMATION: HIV-1 TAT protein

<400> SEQUENCE: 49

Arg Lys Lys Arg Arg Gln Arg Arg Arg
1               5
```

-continued

```
<210> SEQ ID NO 50
<211> LENGTH: 10
<212> TYPE: PRT
<213> ORGANISM: Artificial Sequence
<220> FEATURE:
<223> OTHER INFORMATION: CPP

<400> SEQUENCE: 50

Gly Arg Lys Lys Arg Arg Gln Arg Arg Arg
1               5                   10

<210> SEQ ID NO 51
<211> LENGTH: 8
<212> TYPE: PRT
<213> ORGANISM: Artificial Sequence
<220> FEATURE:
<223> OTHER INFORMATION: CPP

<400> SEQUENCE: 51

Arg Arg Arg Arg Arg Arg Arg Arg
1               5

<210> SEQ ID NO 52
<211> LENGTH: 101
<212> TYPE: PRT
<213> ORGANISM: Artificial Sequence
<220> FEATURE:
<223> OTHER INFORMATION: OmoCS*TAT

<400> SEQUENCE: 52

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
    50                  55                  60

Leu Ile Ser Glu Ile Asp Leu Leu Arg Lys Gln Asn Glu Gln Leu Lys
65                  70                  75                  80

His Lys Leu Glu Gln Leu Arg Asn Ser Ala Gly Arg Lys Lys Arg
                85                  90                  95

Arg Gln Arg Arg Arg
            100

<210> SEQ ID NO 53
<211> LENGTH: 99
<212> TYPE: PRT
<213> ORGANISM: Artificial Sequence
<220> FEATURE:
<223> OTHER INFORMATION: OmoCS*LZArg

<400> SEQUENCE: 53

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
    50                  55                  60
```

Leu Ile Ser Glu Ile Asp Leu Leu Arg Lys Gln Asn Glu Gln Leu Lys
65                  70                  75                  80

His Lys Leu Glu Gln Leu Arg Asn Ser Ser Ala Arg Arg Arg Arg
                85                  90                  95

Arg Arg Arg

<210> SEQ ID NO 54
<211> LENGTH: 9
<212> TYPE: PRT
<213> ORGANISM: Artificial Sequence
<220> FEATURE:
<223> OTHER INFORMATION: M1 peptide

<400> SEQUENCE: 54

Pro Ala Ala Lys Arg Val Lys Leu Asp
1               5

<210> SEQ ID NO 55
<211> LENGTH: 11
<212> TYPE: PRT
<213> ORGANISM: Artificial Sequence
<220> FEATURE:
<223> OTHER INFORMATION: M2 peptide

<400> SEQUENCE: 55

Arg Gln Arg Arg Asn Glu Leu Lys Arg Ser Phe
1               5                   10

<210> SEQ ID NO 56
<211> LENGTH: 6
<212> TYPE: PRT
<213> ORGANISM: Artificial Sequence
<220> FEATURE:
<223> OTHER INFORMATION: poly-glycine region

<400> SEQUENCE: 56

Gly Pro Arg Arg Arg Arg
1               5

<210> SEQ ID NO 57
<211> LENGTH: 8
<212> TYPE: PRT
<213> ORGANISM: Artificial Sequence
<220> FEATURE:
<223> OTHER INFORMATION: FLAG-tag

<400> SEQUENCE: 57

Asp Tyr Lys Asp Asp Asp Asp Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Strep-tag

<400> SEQUENCE: 58

Trp Ser His Pro Gln Phe Glu Lys
1               5

<210> SEQ ID NO 59
<211> LENGTH: 9
<212> TYPE: PRT
<213> ORGANISM: Artificial Sequence

```
<220> FEATURE:
<223> OTHER INFORMATION: HA tag

<400> SEQUENCE: 59

Tyr Pro Tyr Asp Val Pro Asp Tyr Ala
1               5

<210> SEQ ID NO 60
<211> LENGTH: 14
<212> TYPE: PRT
<213> ORGANISM: Artificial Sequence
<220> FEATURE:
<223> OTHER INFORMATION: V5 tag

<400> SEQUENCE: 60

Gly Lys Pro Ile Pro Asn Pro Leu Leu Gly Leu Asp Ser Thr
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Tag sequence

<400> SEQUENCE: 61

Ala His Gly His Arg Pro
1               5

<210> SEQ ID NO 62
<211> LENGTH: 21
<212> TYPE: PRT
<213> ORGANISM: Artificial Sequence
<220> FEATURE:
<223> OTHER INFORMATION: tag sequence
<220> FEATURE:
<221> NAME/KEY: MISC_FEATURE
<222> LOCATION: (19)..(20)
<223> OTHER INFORMATION: Xaa can be any natural occurring amino acid

<400> SEQUENCE: 62

Pro Ile His Asp His Asp His Pro His Leu Val Ile His Ser Gly Met
1               5                   10                  15

Thr Cys Xaa Xaa Cys
            20

<210> SEQ ID NO 63
<211> LENGTH: 90
<212> TYPE: PRT
<213> ORGANISM: Artificial Sequence
<220> FEATURE:
<223> OTHER INFORMATION: Polypeptide

<400> SEQUENCE: 63

Thr Glu Glu Asn Val Lys Arg Arg Thr His Asn Val Leu Glu Arg Gln
1               5                   10                  15

Arg Arg Asn Glu Leu Lys Arg Ser Phe Phe Ala Leu Arg Asp Gln Ile
            20                  25                  30

Pro Glu Leu Glu Asn Asn Glu Lys Ala Pro Lys Val Val Ile Leu Lys
        35                  40                  45

Lys Ala Thr Ala Tyr Ile Leu Ser Val Gln Ala Glu Thr Gln Lys Leu
    50                  55                  60
```

```
Ile Ser Glu Ile Asp Leu Leu Arg Lys Gln Asn Glu Gln Leu Lys His
 65                 70                  75                  80

Lys Leu Glu Gln Leu Arg Asn Ser Ala Ala
                 85                  90

<210> SEQ ID NO 64
<211> LENGTH: 91
<212> TYPE: PRT
<213> ORGANISM: Artificial Sequence
<220> FEATURE:
<223> OTHER INFORMATION: OmoCA

<400> SEQUENCE: 64

Met Thr Glu Glu Asn Val Lys Arg Arg Thr His Asn Val Leu Glu Arg
 1               5                  10                  15

Gln Arg Arg Asn Glu Leu Lys Arg Ser Phe Phe Ala Leu Arg Asp Gln
                 20                  25                  30

Ile Pro Glu Leu Glu Asn Asn Glu Lys Ala Pro Lys Val Val Ile Leu
             35                  40                  45

Lys Lys Ala Thr Ala Tyr Ile Leu Ser Val Gln Ala Glu Thr Gln Lys
         50                  55                  60

Leu Ile Ser Glu Ile Asp Leu Leu Arg Lys Gln Asn Glu Gln Leu Lys
 65                 70                  75                  80

His Lys Leu Glu Gln Leu Arg Asn Ser Ala Ala
                 85                  90
```